US012751673B2

(12) United States Patent
Liu et al.

(10) Patent No.: US 12,751,673 B2
(45) Date of Patent: Oct. 6, 2026

(54) PHYSIOLOGICAL ELECTRIC SIGNAL CLASSIFICATION PROCESSING METHOD AND APPARATUS, COMPUTER DEVICE AND STORAGE MEDIUM

(71) Applicant: TENCENT TECHNOLOGY (SHENZHEN) COMPANY LIMITED, Shenzhen (CN)

(72) Inventors: Luyan Liu, Shenzhen (CN); Kai Ma, Shenzhen (CN); Yefeng Zheng, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 974 days.

(21) Appl. No.: 18/076,098

(22) Filed: Dec. 6, 2022

(65) Prior Publication Data

US 2023/0101539 A1 Mar. 30, 2023

Related U.S. Application Data

(63) Continuation of application No. PCT/CN2022/079832, filed on Mar. 9, 2022.

(30) Foreign Application Priority Data

Mar. 11, 2021 (CN) ......................... 202110262967.7

(51) Int. Cl.
*A61B 5/00* (2006.01)
*A61B 5/117* (2016.01)
(Continued)

(52) U.S. Cl.
CPC ............ *A61B 5/7267* (2013.01); *A61B 5/117* (2013.01); *G06F 18/24147* (2023.01); *A61B 5/369* (2021.01)

(58) Field of Classification Search
CPC ......................... A61B 5/7267; G06F 18/24147
See application file for complete search history.

(56) References Cited

U.S. PATENT DOCUMENTS 10,531,801 B2 * 1/2020 Cheng ................ A61B 5/02411
12,462,199 B2 * 11/2025 Ukil .......................... G06N 5/01
(Continued)

FOREIGN PATENT DOCUMENTS

CN 105989266 A 10/2016
CN 110881969 A 3/2020
(Continued)

OTHER PUBLICATIONS

The World Intellectual Property Organization (WIPO) International Search Report for PCT/CN2022/079832 May 26, 2022 6 Pages (including translation).
(Continued)

*Primary Examiner* — Jay M. Patel
(74) *Attorney, Agent, or Firm* — Anova Law Group, PLLC

(57) ABSTRACT

A physiological electric signal classification processing method includes: performing data alignment on an initial physiological electric signal corresponding to a target user identity based on target signal spatial information corresponding to the target user identify to obtain a target physiological electric signal; performing spatial feature extraction on the target physiological electric signal based on a target spatial filtering matrix to obtain a target spatial feature, the target spatial filtering matrix being generated based on target training physiological electric signals corresponding to a plurality of training user identities respectively and training labels corresponding to the target training physiological electric signals, the target training physiological electric signals being obtained by performing data alignment on initial training physiological electric signals based
(Continued)

on training signal spatial information corresponding to the training user identities; and obtaining a classification result corresponding to the initial physiological electric signal based on the target spatial feature.

19 Claims, 13 Drawing Sheets

(51) Int. Cl.

*A61B 5/369* (2021.01)
*G06F 18/2413* (2023.01)

(56) References Cited

U.S. PATENT DOCUMENTS

| | | | | |
|---|---|---|---|---|
| 2014/0018694 | A1* | 1/2014 | Ang | A61N 1/36003 607/48 |
| 2016/0210534 | A1* | 7/2016 | Padubrin | G06T 7/12 |
| 2017/0085862 | A1* | 3/2017 | McGarry | H03M 7/3059 |
| 2023/0054751 | A1 | 2/2023 | Liu et al. | |

FOREIGN PATENT DOCUMENTS

| | | | |
|---|---|---|---|
| CN | 111325289 | A | 6/2020 |
| CN | 111466909 | A | 7/2020 |
| CN | 111728609 | A | 10/2020 |
| CN | 111832427 | A | 10/2020 |
| CN | 111931646 | A | 11/2020 |
| CN | 112200066 | A | 1/2021 |
| CN | 113705296 | A | 11/2021 |
| KR | 20190030612 | A | 3/2019 |

OTHER PUBLICATIONS

He He et al., "Transfer Learning for Brain—Computer Interfaces: A Euclidean Space Data Alignment Approach". 2019, IEEE Transactions on Biomedical Engineering.

Xingliang Tang et al., "Conditional Adversarial Domain Adaptation Neural Network for Motor Imagery EEG Decoding". 2020, 22(1): 96, Entropy.

He He et al., "Different Set Domain Adaptation for Brain-Computer Interfaces: A Label Alignment Approach" . 2020, 28 (5): 1091-1108, IEEE Transactions on Neural Systems and Rehabilitation Engineering.

China National Intellectual Property Administration (CNIPA) Office Action 1 for Application No. 202110262967.7, Mar. 21, 2025 12 Pages (including translation).

Li Ming'ai Li et al., "Feature Extraction Method of Brain Electrical Signal Based on Improved CSSD." Journal of Beijing University of Technology 39.7 (2013): 1021-1028.

Xiaolin Hong et al. "Dynamic joint domain adaptation network for motor imagery classification." IEEE Transactions on Neural Systems and Rehabilitation Engineering 29 (2021): 556-565.

* cited by examiner

PHYSIOLOGICAL ELECTRIC SIGNAL CLASSIFICATION PROCESSING METHOD AND APPARATUS, COMPUTER DEVICE AND STORAGE MEDIUM

CROSS-REFERENCES TO RELATED APPLICATIONS

This application is a continuation application of PCT Patent Application No. PCT/CN2022/079832, entitled “ELECTROPHYSIOLOGICAL SIGNAL CLASSIFICATION PROCESSING METHOD AND APPARATUS, COMPUTER DEVICE AND STORAGE MEDIUM” and filed on Mar. 9, 2022, which claims priority to Chinese Patent Application No. 202110262967.7, entitled “PHYSIOLOGICAL ELECTRIC SIGNAL CLASSIFICATION PROCESSING METHOD AND APPARATUS, COMPUTER DEVICE AND STORAGE MEDIUM” and filed with the National Intellectual Property Administration, PRC on Mar 11, 2021, the entire contents of both of which are incorporated herein by reference .

FIELD OF THE TECHNOLOGY

The present disclosure relates to the technical field of computers, and in particular, to a physiological electric signal classification processing method and apparatus, a computer device and a storage medium.

BACKGROUND OF THE DISCLOSURE

With the development of computer technology, deep learning technology has shown obvious advantages in computer vision, speech recognition, natural language processing and other fields. Therefore, the deep learning technology has gradually been introduced into the classification task of physiological electric signals by researchers.

Physiological electric signals can reflect human physiological activities. However, due to different responses of different people to physiological activities, physiological electric signals vary greatly among subjects. In the traditional technology, the classification of physiological electric signals is usually based on a transfer learning method. However, transfer learning is a method to improve the learning performance of the target domain by using source domain information. When training a model, it needs to use the physiological electric signals of both source domain subjects and target domain subjects at the same time to train a classification model suitable for the target domain subjects, which is cumbersome to operate.

SUMMARY

The embodiments of the present disclosure provide a physiological electric signal classification processing method and apparatus, a computer device and a storage medium.

A physiological electric signal classification processing method, performed by a computer device, the method including: acquiring an initial physiological electric signal corresponding to a target user identity; performing data alignment on the initial physiological electric signal based on target signal spatial information corresponding to the target user identify to obtain a target physiological electric signal; performing spatial feature extraction on the target physiological electric signal based on a target spatial filtering matrix to obtain a target spatial feature, the target spatial filtering matrix being generated based on target training physiological electric signals corresponding to a plurality of training user identities respectively and training labels corresponding to the target training physiological electric signals, the target training physiological electric signals being obtained by performing data alignment on initial training physiological electric signals based on training signal spatial information corresponding to the training user identities; and obtaining a classification result corresponding to the initial physiological electric signal based on the target spatial feature.

A physiological electric signal classification processing apparatus, the apparatus including: a signal acquisition module configured to acquire an initial physiological electric signal corresponding to a target user identity; a data alignment module configured to perform data alignment on the initial physiological electric signal based on target signal spatial information corresponding to the target user identify to obtain a target physiological electric signal; a feature extraction module configured to perform spatial feature extraction on the target physiological electric signal based on a target spatial filtering matrix to obtain a target spatial feature, the target spatial filtering matrix being generated based on target training physiological electric signals corresponding respectively to a plurality of training user identities and training labels corresponding to the target training physiological electric signals, the target training physiological electric signals being obtained by performing data alignment on initial training physiological electric signals based on training signal spatial information corresponding to the training user identities; and a signal classification module configured to obtain a classification result corresponding to the initial physiological electric signal based on the target spatial feature.

A physiological electric signal classification processing method, performed by a computer device, the method including: acquiring initial training physiological electric signals corresponding to a plurality of training user identifies respectively, the initial training physiological electric signals carrying training labels; performing data alignment on a corresponding initial training physiological electric signal based on training signal spatial information corresponding to the same training user identity to obtain a target training physiological electric signal corresponding to each training user identity; generating a target spatial filtering matrix based on a signal difference between target training physiological electric signals corresponding to different training labels; performing spatial feature extraction on each target training physiological electric signal based on the target spatial filtering matrix to obtain a training spatial feature corresponding to each target training physiological electric signal; and performing model training on an initial physiological electric signal classification model based on the training spatial feature and training label corresponding to each target training physiological electric signal until a convergence condition is met to obtain a target physiological electric signal classification model.

A physiological electric signal classification processing apparatus, the apparatus including: a training data acquisition module configured to acquire initial training physiological electric signals corresponding to a plurality of training user identifies respectively, the initial training physiological electric signals carrying training labels; a training data alignment module configured to perform data alignment on a corresponding initial training physiological electric signal based on training signal spatial information corresponding to the same training user identity to obtain a target training physiological electric signal corresponding to each training user identity; a target spatial filtering matrix generation module configured to generate a target spatial filtering matrix based on a signal difference between target training physiological electric signals corresponding to different training labels; a training feature extraction module configured to perform spatial feature extraction on each target training physiological electric signal based on the target spatial filtering matrix to obtain a training spatial feature corresponding to each target training physiological electric signal; and a classification model training module configured to perform model training on an initial physiological electric signal classification model based on the training spatial feature and training label corresponding to each target training physiological electric signal until a convergence condition is met to obtain a target physiological electric signal classification model.

A computer device is provided, including a memory and one or more processors, the memory storing computer-readable instructions, the computer-readable instructions, when executed by the one or more processors, causing the one or more processors to perform the steps of the method for classification processing of an electrophysiological signal described above.

One or more non-transitory computer-readable storage media are provided, storing computer-readable instructions, the computer-readable instructions, when executed by one or more processors, causing the one or more processors to perform the steps of the method for classification processing of an electrophysiological signal described above.

Details of one or more embodiments of the present disclosure are provided in the accompanying drawings and descriptions below. Other features, objectives, and advantages of the present disclosure are illustrated in the specification, the accompanying drawings, and the claims.

BRIEF DESCRIPTION OF THE DRAWINGS

To describe the technical solutions in embodiments of the present disclosure more clearly, the following briefly describes the accompanying drawings required for describing the embodiments. Apparently, the accompanying drawings in the following description show merely some embodiments of the present disclosure, and a person of ordinary skill in the art may derive other drawings from these accompanying drawings without creative efforts.

DESCRIPTION OF EMBODIMENTS

To make the objectives, technical solutions, and advantages of the present disclosure clearer and more understandable, the present disclosure is further described in detail below with reference to accompanying drawings and embodiments. It is to be understood that the specific embodiments described herein are only used for explaining the present disclosure, and are not used for limiting the present disclosure.

AI technology is a comprehensive discipline, covering a wide range of fields including both a hardware-level technology and a software-level technology. Basic AI technologies generally include technologies such as a sensor, a dedicated AI chip, cloud computing, distributed storage, a big data processing technology, an operating/interaction system, and electromechanical integration. AI software technologies mainly include a computer vision technology, a speech processing technology, a natural language processing technology, machine learning/deep learning, and the like.

Machine learning (ML) is a multi-field interdiscipline and relates to a plurality of disciplines such as the probability theory, statistics, the approximation theory, convex analysis, and the algorithm complexity theory. ML specializes in studying how a computer simulates or implements a human learning behavior to acquire new knowledge or skills, and reorganize an existing knowledge structure, so as to keep improving its performance. The ML is the core of the AI, is a basic way to make the computer intelligent, and is applied to various fields of AI. The ML and DL generally include technologies such as an artificial neural network, a belief network, reinforcement learning, transfer learning, inductive learning, and learning from demonstrations.

The solutions provided in the embodiments of the present disclosure involve technologies such as ML of AI, big data processing and are specifically described by using the following embodiments.

Figure 1:
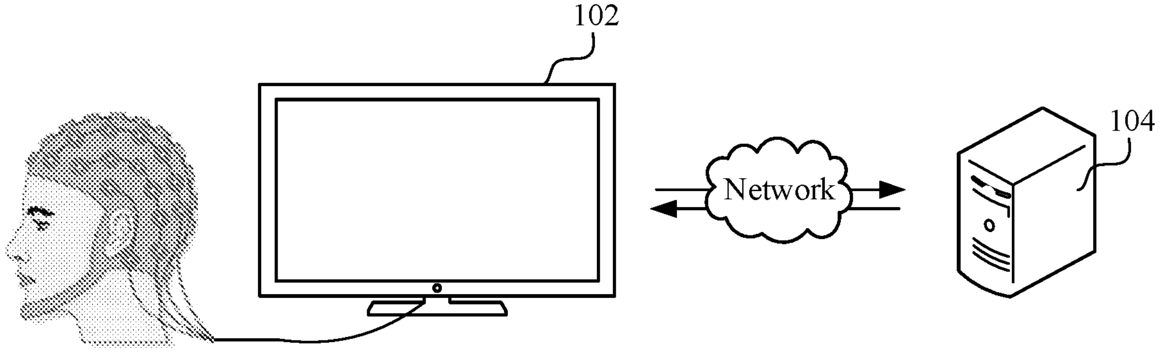
FIG. 1 is a diagram of an application environment of a physiological electric signal classification processing method according to an embodiment.

A physiological electric signal classification processing method provided in the present disclosure may be applied to an application environment shown in FIG. 1. A terminal 102 communicates with a server 104 through a network. The terminal 102 may be, but not limited to, a desktop computer, a notebook computer, a smartphone, a tablet computer, an on-board terminal, a portable wearable device, and a physiological electric signal acquisition device. The server 104 may be implemented by an independent server or a server cluster including a plurality of servers or a cloud server.

Both the terminal 102 and the server 104 may be used independently to perform the physiological electric signal classification processing method provided in the embodiments of the present disclosure.

For example, the terminal firstly acquires an initial to-be-classified physiological electric signal (also called initial physiological electric signal) corresponding to a target user identity, and performs data alignment on the initial to-be-classified physiological electric signal based on target signal spatial information corresponding to the target user identify to obtain a target to-be-classified physiological electric signal (also called target physiological electric signal). Then, the terminal acquires a target spatial filtering matrix, and performs spatial feature extraction on the target to-be-classified physiological electric signal based on the target spatial filtering matrix to obtain a to-be-classified spatial feature (also called target spatial feature). The target spatial filtering matrix is generated based on target training physiological electric signals corresponding to a plurality of training user identities respectively and training labels corresponding to the target training physiological electric signals. The target training physiological electric signals are obtained by performing data alignment on initial training physiological electric signals based on training signal spatial information corresponding to the training user identities. Finally, the terminal can obtain a classification result corresponding to the initial to-be-classified physiological electric signal based on the to-be-classified spatial feature.

The server acquires initial training physiological electric signals corresponding to a plurality of training user identifies respectively. Each initial training physiological electric signal carries a corresponding training label. The server performs data alignment on a corresponding initial training physiological electric signal based on training signal spatial information corresponding to the same training user identity to obtain a target training physiological electric signal corresponding to each training user identity, and generates a target spatial filtering matrix based on a signal difference between target training physiological electric signals corresponding to different training labels. Then, the server performs spatial feature extraction on each target training physiological electric signal based on the target spatial filtering matrix to obtain a training spatial feature corresponding to each target training physiological electric signal, and performs model training on an initial physiological electric signal classification model based on the training spatial feature and training label corresponding to each target training physiological electric signal until the training is completed to obtain a target physiological electric signal classification model.

Both the terminal 102 and the server 104 may be alternatively used in cooperation to perform the physiological electric signal classification processing method provided in the embodiments of the present disclosure.

For example, the server generates a target spatial filtering matrix based on the target training physiological electric signals corresponding to the training user identities respectively and the training label corresponding to each target training physiological electric signal. The terminal acquires a target spatial filtering matrix from the server, and classifies the initial to-be-classified physiological electric signal corresponding to the target user identity based on the target spatial filtering matrix.

The terminal acquires initial training physiological electric signals corresponding to a plurality of training user identifies respectively, and determines a training label corresponding to each initial training physiological electric signal. The server acquires initial training physiological electric signals corresponding to a plurality of training user identifies respectively from the terminal, and performs training based on each initial training physiological electric signal and the corresponding training label to obtain a target spatial filtering matrix and a target physiological electric signal classification model.

In the physiological electric signal classification processing method, firstly data alignment is performed on the corresponding initial physiological electric signal based on the training signal spatial information corresponding to the same training user identity, which can reduce the distribution difference between the physiological electric signals of different training users; and then a universal target spatial filtering matrix is generated based on the target physiological electric signal obtained through data alignment and the corresponding training label, and the spatial feature in physiological electric signal that can be used for distinguishing the category of the physiological electric signal can be extracted through the target spatial filtering matrix. Then, when classifying a physiological electric signal of an unknown user, firstly data alignment is performed on an initial to-be-classified physiological electric signal corresponding to a target user identity based on target signal spatial information corresponding to the target user identity, so as to reduce the distribution difference between the physiological electric signals of the target user and the training user, and then the spatial feature of the target to-be-classified physiological electric signal obtained by data alignment is extracted based on the universal target spatial filtering matrix, so that a classification result corresponding to the initial to-be-classified physiological electric signal can be obtained based on the extracted to-be-classified spatial feature. In this way, the physiological electric signal of the target user can be classified without acquiring it in advance, which is more convenient and efficient.

In addition, the spatial feature of the physiological electric signal that can be used for distinguishing the category of the physiological electric signal can be extracted through the target spatial filtering matrix. In this way, the target spatial filtering matrix and the target physiological electric signal classification model that can be used for classifying the physiological electric signal of the target user can be obtained through training without acquiring the physiological electric signal of the target user in advance. Through the target spatial filtering matrix and the target physiological electric signal classification model, the physiological electric signal of the target user can be classified, which is more convenient and efficient.

Figure 2:
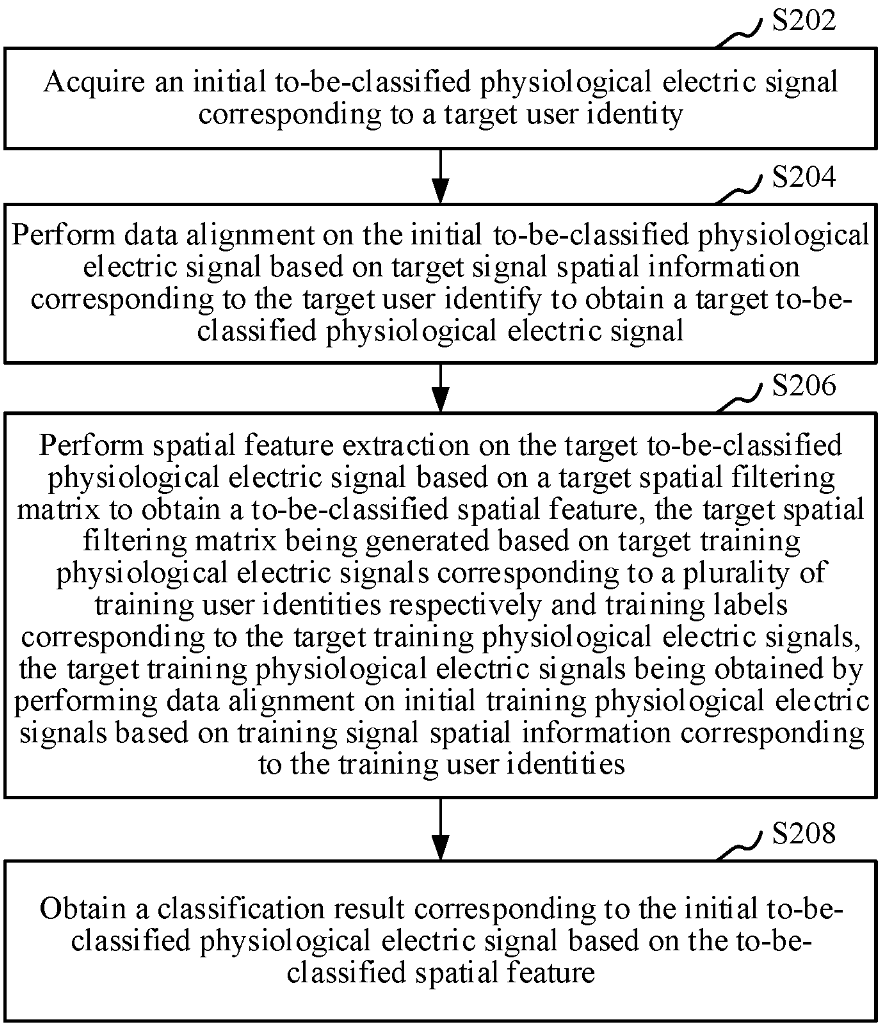
FIG. 2 is a schematic flowchart of a physiological electric signal classification processing method according to an embodiment.

In an embodiment, referring to FIG. 2, a physiological electric signal classification processing method is provided. Description will be made below by taking that the method is applied to a computer device in FIG. 1 as an example. The computer device may be the terminal 102 or the server 104 in FIG. 1. Referring to FIG. 2, the physiological electric signal classification processing method includes the following steps:

Step S202: Acquire an initial to-be-classified physiological electric signal corresponding to a target user identity.

A user identity is an identity used for uniquely identifying a user, which specifically may include a character string of at least one of letters, numbers and symbols. A target user identity refers to a user identity corresponding to a target user. A physiological electric signal refers to a physiological signal presented by current or voltage, which is used for reflecting the electrophysiological activity of nerve cells. A physiological electric signal specifically may be an electroencephalogram signal, an electromyogram signal, an electrocardiograph signal, etc. A to-be-classified physiological electric signal refers to a physiological electric signal to be subjected to signal classification. An initial to-be-classified physiological electric signal refers to a to-be-classified physiological electric signal which has not been subjected to data alignment.

Specifically, the computer device may acquire an initial to-be-classified physiological electric signal corresponding to a target user identity locally or from other terminals and servers. It is to be understood that a physiological electric signal acquisition device may associate an acquired physiological electric signal with a corresponding user when acquiring the physiological electric signal. Specifically, an association relationship may be established between the physiological electric signal and the user identity of the corresponding user, so that the physiological electric signals of different users can be effectively distinguished based on the user identities corresponding to the physiological electric signals.

In an embodiment, the to-be-classified physiological electric signal may be a physiological electric signal acquired in real time. The physiological electric signal acquisition device may acquire the physiological electric signal in real time, and the computer device may classify the latest physiological electric signal in real time to obtain a corresponding classification result. Of course, the to-be-classified physiological electric signal may also be a physiological electric signal acquired at historical time. The physiological electric signal acquired in real time by the physiological electric signal acquisition device may be stored in a database of the terminal or server. The computer device may acquire a physiological electric signal acquired at historical time from the database, and classify the physiological electric signal to obtain a corresponding classification result.

In an embodiment, the initial to-be-classified physiological electric signal may be an original physiological electric signal, that is, the physiological electric signal acquired by the physiological electric signal acquisition device is directly used as the initial to-be-classified physiological electric signal. The initial to-be-classified physiological electric signal may also be a preprocessed physiological electric signal. For example, the physiological electric signal acquired by the physiological electric signal acquisition device is subjected to band-pass filtering, and the physiological electric signal after filtering is used as the initial to-be-classified physiological electric signal. The accuracy of classification can be effectively improved by firstly performing band-pass filtering on the physiological electric signal to filter out the noise, and then performing classification processing on the physiological electric signals after band-pass filtering.

Step S204: Perform data alignment on the initial to-be-classified physiological electric signal based on target signal spatial information corresponding to the target user identify to obtain a target to-be-classified physiological electric signal.

Target signal spatial information refers to signal spatial information corresponding to a target user. Signal spatial information refers to signal distribution information generated based on a plurality of physiological electric signals of a user in European space, which is used for characterizing an overall distribution situation of a plurality of physiological electric signals of a user. Different users correspond to different signal spatial information. Data alignment refers to mapping the initial to-be-classified physiological electric signal to a target range to obtain the target to-be-classified physiological electric signal, so that the target to-be-classified physiological electric signal corresponding to each initial to-be-classified physiological electric signal can be located in the same target range, so as to achieve the data alignment of each initial to-be-classified physiological electric signal.

Specifically, the computer device may acquire a plurality of physiological electric signals corresponding to the same user identity, and generate signal spatial information corresponding to the user identity based on the plurality of physiological electric signals. After obtaining an initial to-be-classified physiological electric signal corresponding to a target user identity, the computer device may acquire target signal spatial information corresponding to the target user identity, and perform data alignment on the initial to-be-classified physiological electric signal based on the target signal spatial information to obtain a target to-be-classified physiological electric signal.

In an embodiment, the signal spatial information is updated in real time. For example, once the computer device acquires the physiological electric signal corresponding to the target user identity, it can update the signal spatial information corresponding to the target user identity. It is to be understood that the more the physiological electric signals, the more accurate and reliable the signal spatial information generated.

In an embodiment, the computer device may generate the signal spatial information corresponding to the user identity based on a covariance matrix corresponding to at least one physiological electric signal corresponding to the same user identity. Specifically, a mean value of a covariance matrix corresponding to each physiological electric signal may be used as the signal spatial information. Each physiological electric signal includes channel signals respectively acquired by a plurality of acquisition channels. The covariance matrix corresponding to the physiological electric signal can reflect a correlation between the channel signals and the distribution situation of the channel signals. The mean value of the covariance matrix corresponding to the physiological electric signal can reflect the average correlation between the channel signals and the average distribution situation of the channel signals, the average distribution situation of the channel signals is used as the overall distribution situation of the physiological electric signals.

In an embodiment, the initial to-be-classified physiological electric signal may be a preprocessed physiological electric signal, so the initial to-be-classified physiological electric signal may include initial to-be-classified sub-signals (also called initial sub-signals) corresponding to at least one target frequency band respectively. Correspondingly, the target signal spatial information may include target signal spatial sub-information corresponding to at least one target frequency band. Then, when data alignment is performed on the initial to-be-classified physiological electric signal based on the target signal spatial information, data alignment may be performed on the corresponding initial to-be-classified sub-signal based on the target signal spatial sub-information corresponding to the same target frequency band to obtain target to-be-classified sub-information corresponding to each target frequency band, and the target to-be-classified physiological electric signal can be obtained based on the target to-be-classified sub-information.

Step S206: Perform spatial feature extraction on the target to-be-classified physiological electric signal based on a target spatial filtering matrix to obtain a to-be-classified spatial feature. The target spatial filtering matrix is generated based on target training physiological electric signals corresponding to a plurality of training user identities respectively and training labels corresponding to the target training physiological electric signals. The target training physiological electric signals are obtained by performing data alignment on initial training physiological electric signals based on training signal spatial information corresponding to the training user identities.

The target spatial filtering matrix is a spatial filter used for extracting the spatial feature of the physiological electric signal. The spatial feature with high discrimination can be extracted from the physiological electric signal, and the classification result of the physiological electric signal can be obtained based on the extracted spatial feature. The target spatial filtering matrix is generated based on target training physiological electric signals corresponding to a plurality of training user identities respectively and obtained after data alignment, and training labels corresponding to the target training physiological electric signals. The generated target spatial filtering matrix can maximize the difference between the spatial features corresponding to the physiological electric signals of different categories. Therefore, the spatial feature extracted from the physiological electric signal based on the target spatial filtering matrix can have high discrimination, which is conducive to the classification of the physiological electric signal.

A training user identity refers to a user identity corresponding to a training user. The training user and the target user are different users. Training signal spatial information refers to signal spatial information corresponding to a training user. A training physiological electric signal refers to a physiological electric signal corresponding to a training user, and is a physiological electric signal with a classification result known. A training label refers to a classification result corresponding to a training physiological electric signal. An initial training physiological electric signal refers to a training physiological electric signal which has not been subjected to data alignment. A target training physiological electric signal refers to a training physiological electric signal which has been subjected to data alignment.

Specifically, the computer device acquires initial training physiological electric signals corresponding to a plurality of training user identities respectively and a training label corresponding to each initial training physiological electric signal, and performs data alignment on the corresponding initial training physiological electric signal based on the training signal spatial information corresponding to the same training user identity to obtain a target training physiological electric signal corresponding to each initial training physiological electric signal. For example, data alignment is performed on an initial training physiological electric signal corresponding to a training user A based on the training signal spatial information corresponding to the training user A to obtain a target training physiological electric signal corresponding to the initial training physiological electric signal of the training user A. Then, the computer device generates a target spatial filtering matrix based on the target training physiological electric signals corresponding to the training user identities respectively and the training label corresponding to each target training physiological electric signal. Then, after the target to-be-classified physiological electric signal is obtained, the computer device may extract the spatial feature of the target to-be-classified physiological electric signal based on the target spatial filtering matrix to obtain a to-be-classified spatial feature, so that a classification result corresponding to the initial to-be-classified physiological electric signal can be obtained based on the o-be-classified spatial feature.

It is to be understood that the target spatial filtering matrix is a universal spatial filtering matrix, which can be applied to the physiological electric signal corresponding to the target user identity, as well as the physiological electric signal corresponding to the training user identity.

In an embodiment, the target spatial filtering matrix may include at least one target spatial filtering sub-matrix. Spatial feature extraction is performed on the target to-be-classified physiological electric signal based on each target spatial filtering sub-matrix, each to-be-classified spatial sub-feature (also called target spatial sub-feature) can be obtained, and a to-be-classified spatial feature can be obtained based on each o-be-classified spatial sub-feature.

In an embodiment, performing the spatial feature extraction to the target to-be-classified physiological electric signal based on the target spatial filtering matrix may specifically be performing signal projection to the target to-be-classified physiological electric signal based on the target spatial filtering matrix, and obtaining the to-be-classified spatial feature based on a signal projection result. Correspondingly, when the target spatial filtering matrix includes at least one target spatial filtering sub-matrix, signal projection is performed on the target to-be-classified physiological electric signal based on each target spatial filtering sub-matrix, and the to-be-classified spatial feature is obtained based on each signal projection result.

Step S208: Obtain a classification result corresponding to the initial to-be-classified physiological electric signal based on the to-be-classified spatial feature.

Specifically, since the to-be-classified spatial feature has certain discrimination, the computer device can obtain a classification result corresponding to the initial to-be-classified physiological electric signal based on the to-be-classified spatial feature.

In an embodiment, the computer device may perform data processing on the to-be-classified spatial feature based on a user-defined formula to obtain a classification result.

In an embodiment, a machine learning model may be used for performing classification processing on the physiological electric signal, specifically training a classifier for classifying the spatial feature. The computer device may perform spatial feature extraction on each target training physiological electric signal based on the target spatial filtering matrix to obtain a training spatial feature corresponding to each target training physiological electric signal, and perform training based on the training spatial feature and training label corresponding to each target training physiological electric signal to obtain a target physiological electric signal classification model. Then, when the classification result corresponding to the initial to-be-classified physiological electric signal is obtained based on the to-be-classified spatial feature, the computer device may acquire the trained target physiological electric signal classification model and input the to-be-classified spatial feature into the target physiological electric signal classification model, and the target physiological electric signal classification model outputs the classification result. The classifier may be a logistic regression classifier, such as a Support Vector Machine (SVM).

In an embodiment, for different classification tasks, different target spatial filtering matrices may be generated, and different target physiological electric signal classification models may also be generated. For example, when the physiological electric signals are electroencephalogram signals, the classification tasks for the electroencephalogram signals may include emotion classification, motion imagination classification, attention classification, etc. Then, a spatial filtering matrix and an electroencephalogram signal classification model specifically used for performing emotion classification on electroencephalogram signals may be trained based on electroencephalogram signals with a training label which is an emotion classification result; a spatial filtering matrix and an electroencephalogram signal classification model specifically used for performing motion imagination classification on electroencephalogram signals may be trained based on electroencephalogram signals with a training label which is a motion imagination classification result; a spatial filtering matrix and an electroencephalogram signal classification model specially used for performing attention classification on electroencephalogram signals may be trained based on electroencephalogram signals with a training label which is an attention classification result. When the physiological electric signals are electromyogram signals, the classification tasks for the electromyogram signals may include emotion classification, muscle state imagination classification, etc. Then, a spatial filtering matrix and an electromyogram signal classification model specifically used for performing emotion classification on electromyogram signals may be trained based on electromyogram signals with a training label which is an emotion classification result; a spatial filtering matrix and an electromyogram signal classification model specifically used for performing muscle state classification on electromyogram signals may be trained based on electromyogram signals with a training label which is a muscle state classification result.

In an embodiment, the classification result of the electroencephalogram signal in the motion imagination classification task can be used for helping the disabled achieve object grasping, artificial limb control and other functions. During motion imagination, a user will generate an electroencephalogram signal with a certain characteristic. For example, the electroencephalogram signals of the user imagining left hand motion and right hand motion are different. The physiological electric signal classification processing method provided by the present disclosure can be applied to an online brain-computer interface system, so as to accurately perform motion imagination classification on electroencephalogram signals, thereby helping the disabled to achieve object grasping, artificial limb control and other functions.

In the physiological electric signal classification processing method, firstly data alignment is performed on the corresponding initial physiological electric signal based on the training signal spatial information corresponding to the same training user identity, which can reduce the distribution difference between the physiological electric signals of different training users; and then a universal target spatial filtering matrix is generated based on the target physiological electric signal obtained through data alignment and the corresponding training label, and the spatial feature in physiological electric signal that can be used for distinguishing the category of the physiological electric signal can be extracted through the target spatial filtering matrix. Then, when classifying a physiological electric signal of an unknown user, firstly data alignment is performed on an initial to-be-classified physiological electric signal corresponding to a target user identity based on target signal spatial information corresponding to the target user identity, so as to reduce the distribution difference between the physiological electric signals of the target user and the training user, and then the spatial feature of the target to-be-classified physiological electric signal obtained by data alignment is extracted based on the universal target spatial filtering matrix, so that a classification result corresponding to the initial to-be-classified physiological electric signal can be obtained based on the extracted to-be-classified spatial feature. In this way, the physiological electric signal of the target user can be classified without acquiring it in advance, which is more convenient and efficient.

In an embodiment, acquiring an initial to-be-classified physiological electric signal corresponding to a target user identity includes:

acquiring a candidate to-be-classified physiological electric signal (also called candidate physiological electric signal) corresponding to the target user identity; performing signal extraction of at least one target frequency band for the candidate to-be-classified physiological electric signal to obtain an initial to-be-classified sub-signal corresponding to the candidate to-be-classified physiological electric signal at each target frequency band; obtaining the initial to-be-classified physiological electric signal based on each initial to-be-classified sub-signal.

Specifically, a candidate to-be-classified physiological electric signal refers to a to-be-classified physiological electric signal which has not been subjected to any data processing. The computer device may acquire a candidate to-be-classified physiological electric signal corresponding to the target user identity, and perform band-pass filtering on the candidate to-be-classified physiological electric signal, that is, perform signal extraction of at least one target frequency band for the candidate to-be-classified physiological electric signal to obtain an initial to-be-classified sub-signal corresponding to the candidate to-be-classified physiological electric signal at each target frequency band. Then, all initial to-be-classified sub-signals form the initial to-be-classified physiological electric signal.

In an embodiment, there may or may not be overlap between different target frequency bands. For example, target frequency bands may be divided into 4-8 Hz, 8-12 Hz, 12-16 Hz and 16-20 Hz, and there is no overlap between the target frequency bands. Target frequency bands may also be divided into 4-8 Hz, 6-10 Hz, 8-12 Hz, 10-14 Hz, 12-16 Hz, 14-18 Hz and 16-20 Hz, and there is an overlap between the target frequency bands.

In this embodiment, through the signal extraction of the target frequency band, not only the noise and some invalid signals in the to-be-classified physiological electric signal can be filtered, but also the to-be-classified physiological electric signal can be subdivided, and the big data can be subdivided into small data for subsequent processing, which helps to improve the classification accuracy of the physiological electric signal.

Figure 3:
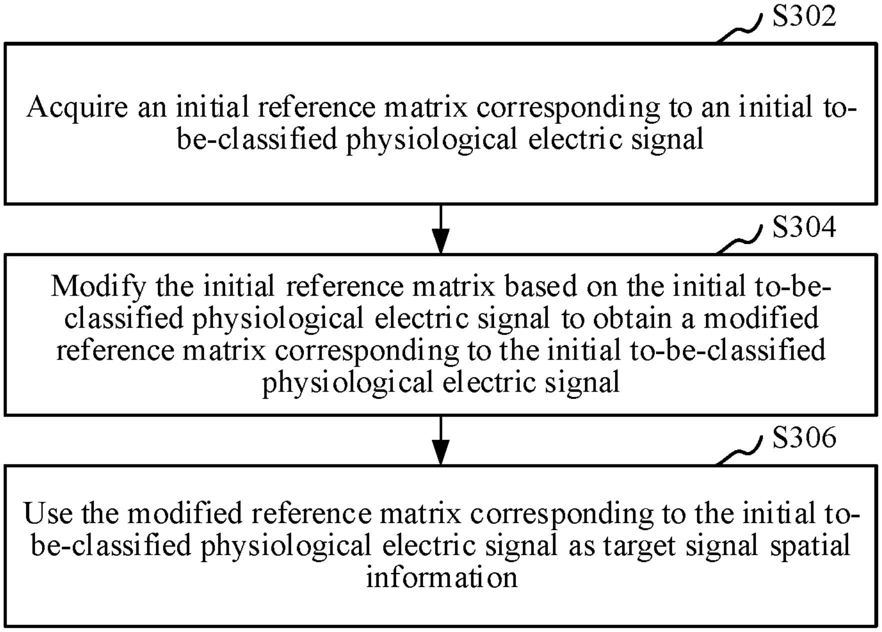
FIG. 3 is a schematic flowchart of determining target signal spatial information according to an embodiment.

In an embodiment, referring to FIG. 3, before performing data alignment on the initial to-be-classified physiological electric signal based on target signal spatial information corresponding to the target user identify to obtain a target to-be-classified physiological electric signal, the method further includes:

Step S302: Acquire an initial reference matrix corresponding to the initial to-be-classified physiological electric signal.

Step S304: Modify the initial reference matrix based on the initial to-be-classified physiological electric signal to obtain a modified reference matrix corresponding to the initial to-be-classified physiological electric signal.

Step S306: Use the modified reference matrix corresponding to the initial to-be-classified physiological electric signal as the target signal spatial information.

The reference matrix is used for performing data alignment on the physiological electric signal. The initial reference matrix corresponding to the initial to-be-classified physiological electric signal is generated based on the classified physiological electric signals corresponding to the target user identity, which is used for performing data alignment on a previous to-be-classified physiological electric signal (also called previous physiological electric signal) corresponding to the target user identity. The modified reference matrix corresponding to the initial to-be-classified physiological electric signal is generated based on the initial to-be-classified physiological electric signal and the initial reference matrix, which is used for performing data alignment on the initial to-be-classified physiological electric signal.

Specifically, the computer device can perform data alignment on the physiological electric signal based on the reference matrix to reduce the distribution difference between the physiological electric signals of different users. The computer device may acquire the initial reference matrix corresponding to the initial to-be-classified physiological electric signal, modify the initial reference matrix based on the initial to-be-classified physiological electric signal to obtain a modified reference matrix corresponding to the initial to-be-classified physiological electric signal, use the modified reference matrix as the target signal spatial information corresponding to the target user identity, and then perform data alignment on the initial to-be-classified physiological electric signal based on the modified reference matrix to obtain a target to-be-classified physiological electric signal.

In an embodiment, the initial reference matrix is a modified reference matrix corresponding to a previous to-be-classified physiological electric signal corresponding to the target user identity.

Specifically, In the classification process of the physiological electric signal, the reference matrix is gradually modified. Every time the computer device acquires a to-be-classified physiological electric signal corresponding to the target user identity, it will modify the reference matrix. Therefore, the initial reference matrix corresponding to the current to-be-classified physiological electric signal of the target user is the modified reference matrix corresponding to the previous to-be-classified physiological electric signal of the target user. In this way, the reference matrix is continuously modified based on the new data, and the reference matrix used for data alignment will become more accurate and reliable, thus helping to improve the classification accuracy of the physiological electric signal.

For example, when the to-be-classified physiological electric signal of the target user is acquired for the first time, the computer device may initialize the reference matrix corresponding to the target user to obtain an initial reference matrix A1, modify the initial reference matrix A1 based on the to-be-classified physiological electric signal to obtain a modified reference matrix B1, and use the modified reference matrix B1 as the target signal spatial information corresponding to the to-be-classified physiological electric signal. When a new to-be-classified physiological electric signal of the target user is acquired, the computer device uses the modified reference matrix B1 as an initial reference matrix A2, modify the initial reference matrix A2 based on the to-be-classified physiological electric signal to obtain a modified reference matrix B2, and use the modified reference matrix B2 as the target signal spatial information corresponding to the to-be-classified physiological electric signal. By analogy, the reference matrix is gradually modified in the process classification of the physiological electric signal. Initializing the reference matrix corresponding to the target user may specifically be initializing the reference matrix corresponding to the target user to 0.

In this embodiment, the initial reference matrix is modified based on the initial to-be-classified physiological electric signal to obtain a modified reference matrix corresponding to the initial to-be-classified physiological electric signal, and the modified reference matrix corresponding to the initial to-be-classified physiological electric signal is used as the target signal spatial information. In this way, the reference matrix used for data alignment continuously fuses the relevant information of the current physiological electric signal, which can more accurately reflect the overall distribution situation of a plurality of physiological electric signals of the target user.

Figure 4:
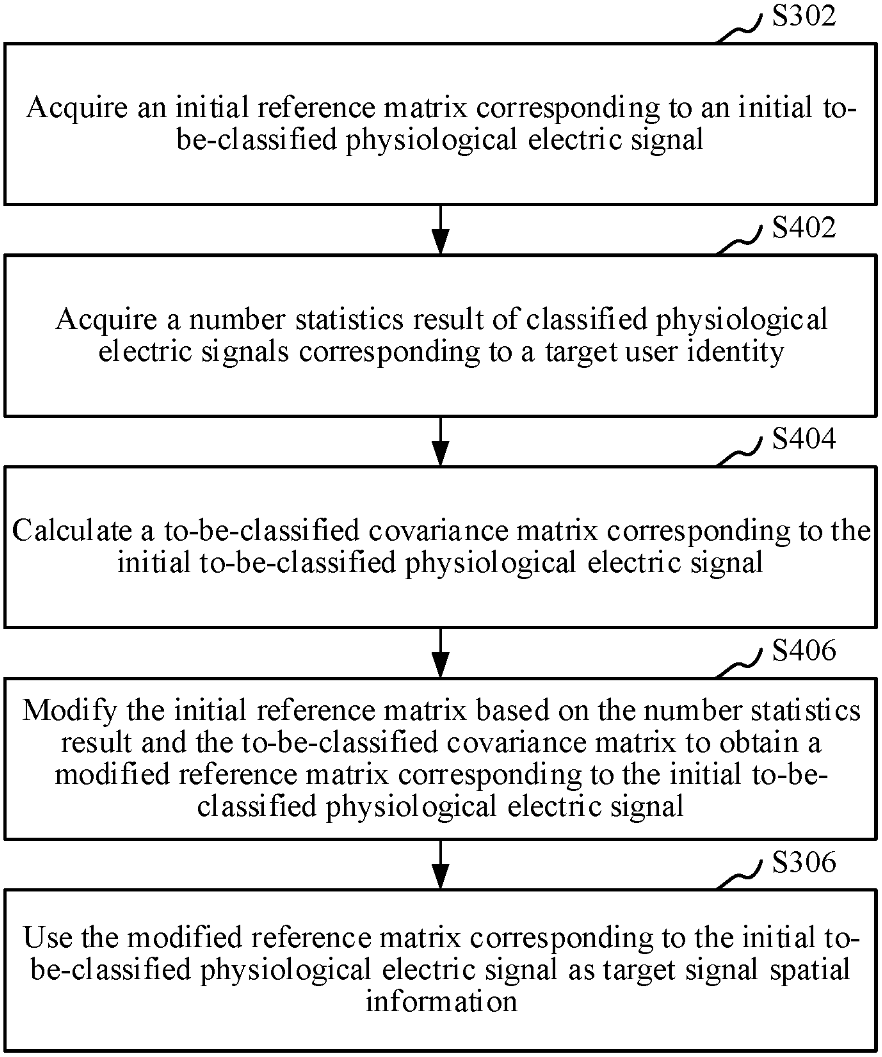
FIG. 4 is a schematic flowchart of determining target signal spatial information according to another embodiment.

In an embodiment, as shown in FIG. 4, modifying the initial reference matrix based on the initial to-be-classified physiological electric signal to obtain a modified reference matrix corresponding to the initial to-be-classified physiological electric signal includes the following steps:

Step S402: Acquire a number statistics result of classified physiological electric signals corresponding to the target user identity.

Step S404: Calculate a to-be-classified covariance matrix corresponding to the initial to-be-classified physiological electric signal.

Step S406: Modify the initial reference matrix based on the number statistics result and the to-be-classified covariance matrix to obtain a modified reference matrix corresponding to the initial to-be-classified physiological electric signal.

The physiological electric signal is a multi-channel signal, including channel signals corresponding to each acquisition channel. The physiological electric signal acquisition device includes a plurality of acquisition channels (i.e., electrodes), and different acquisition channels are used for acquiring physiological electric signals at different positions. The covariance matrix corresponding to the physiological electric signal is a matrix composed of the covariance between the channel signals in the physiological electric signal. The to-be-classified covariance matrix refers to a covariance matrix corresponding to the initial to-be-classified physiological electric signal.

Specifically, the reference matrix may be a covariance matrix, and the covariance matrix of data can reflect the correlation between data elements. Therefore, when the initial reference matrix is modified, a reference can be made to the to-be-classified covariance matrix corresponding to the initial to-be-classified physiological electric signal. In addition, the reference matrix is continuously updated based on new physiological electric signals. Therefore, when the initial reference matrix is modified, a reference can be further made to the number statistics result of the classified physiological electric signals corresponding to the target user identity. Each time the computer device classifies a physiological electric signal of the target user, it will update the number statistics result of the classified physiological electric signals corresponding to the target user identity in time.

When the current initial to-be-classified physiological electric signal is processed, the computer device may calculate the to-be-classified covariance matrix corresponding to the initial to-be-classified physiological electric signal, acquire the number statistics result of the classified physiological electric signals corresponding to the target user identity, and modify the initial reference matrix based on the number statistics result and the to-be-classified covariance matrix to obtain the modified reference matrix corresponding to the initial to-be-classified physiological electric signal.

In an embodiment, the initial reference matrix includes initial reference sub-matrices corresponding to at least one target frequency band respectively, and the initial to-be-classified physiological electric signal includes an initial to-be-classified sub-signal corresponding to the at least one target frequency band. Then, when the initial reference matrix is modified, the initial reference sub-matrix corresponding to each target frequency band is modified independently.

In this embodiment, the initial reference matrix can be modified accurately and effectively based on the number statistics result and the to-be-classified covariance matrix, so data alignment based on the accurate modified reference matrix helps to improve the classification accuracy of the physiological electric signal.

In an embodiment, the initial reference matrix includes initial reference sub-matrices corresponding to at least one target frequency band respectively, and the initial to-be-classified physiological electric signal includes an initial to-be-classified sub-signal corresponding to the at least one target frequency band. Modifying the initial reference matrix based on the number statistics result and the to-be-classified covariance matrix to obtain a modified reference matrix corresponding to the initial to-be-classified physiological electric signal includes:

modifying the corresponding initial reference sub-matrix based on the initial to-be-classified sub-signals corresponding to the same target frequency band and the number statistics result to obtain a modified reference sub-matrix corresponding to each target frequency band; obtaining the modified reference matrix based on each modified reference sub-matrix.

Specifically, if the initial reference matrix includes the initial reference sub-matrices corresponding to at least one target frequency band respectively, the initial reference sub-matrix corresponding to each target frequency band needs to be modified independently. Therefore, the computer device may modify the corresponding initial reference sub-matrix based on the initial to-be-classified sub-signals corresponding to the same target frequency band and the number statistics result to obtain a modified reference sub-matrix corresponding to each target frequency band. Then, the modified reference sub-matrices form the modified reference matrix.

In an embodiment, the initial reference matrix may be modified by adopting the following formula:

$$R_j = \frac{R'_j * N + x_j x_j^T}{N + 1}$$

where $R_j$ represents the modified reference sub-matrix corresponding to the target frequency band j, $$R'_j$$

represents the initial reference sub-matrix corresponding to the target frequency band j, N represents the number statistics result, $x_j$ represents the initial to-be-classified sub-signal corresponding to the target frequency band j, and $$x_j^T$$

represents the transposition of $x_j$.

$$x_j x_j^T$$

can represent the covariance matrix corresponding to $x_j$.

In this embodiment, the initial reference sub-matrix corresponding to each target frequency band is modified independently, which can improve the modification accuracy. Therefore, data alignment and subsequent processing based on the accurate modified reference matrix can be performed to help to improve the classification accuracy of the physiological electric signal.

In an embodiment, the modified reference matrix corresponding to the initial to-be-classified physiological electric signal includes modified reference sub-matrices corresponding to at least one target frequency band respectively, and the initial to-be-classified physiological electric signal includes initial to-be-classified sub-signals corresponding to the at least one target frequency band respectively. Performing data alignment on the initial to-be-classified physiological electric signal based on target signal spatial information corresponding to the target user identify to obtain a target to-be-classified physiological electric signal includes:

fusing the modified reference sub-matrix and the initial to-be-classified sub-signal corresponding to the same target frequency band to obtain a target to-be-classified sub-signal (also called target sub-signal) corresponding to each target frequency band; and obtaining the target to-be-classified physiological electric signal based on each target to-be-classified sub-signal.

Specifically, if no band-pass filtering is performed on the physiological electric signal during the classification of the physiological electric signal, the modified reference matrix and the initial to-be-classified physiological electric signal may be directly fused, so that data alignment is performed on the initial to-be-classified physiological electric signal based on the modified reference matrix to obtain a target to-be-classified physiological electric signal. If band-pass filtering has been performed on the physiological electric signal in the classification process of the physiological electric signal, each target frequency band requires independent data alignment when data alignment is performed. If band-pass filtering has been performed on the physiological electric signal, then the modified reference matrix corresponding to the initial to-be-classified physiological electric signal includes modified reference sub-matrices corresponding to at least one target frequency band respectively, the initial to-be-classified physiological electric signal includes initial to-be-classified sub-signals corresponding to at least one target frequency band respectively, and the computer device may fuse the modified reference sub-matrix and the initial to-be-classified sub-signal corresponding to the same target frequency band to obtain a target to-be-classified sub-signal corresponding to each target frequency band. Then, all target to-be-classified sub-signals form the target to-be-classified physiological electric signal.

In an embodiment, data alignment may be performed by adopting the following formula:

$$\tilde{x}_t = R_j^{-\frac{1}{2}} x_j$$

where $\tilde{x}_j$ represents the target to-be-classified sub-signal corresponding to the target frequency band j, $R_j$ represents the modified reference sub-matrix corresponding to the target frequency band j, and $x_j$ represents the initial to-be-classified sub-signal corresponding to the target frequency band j.

In this embodiment, data alignment is performed on the initial to-be-classified sub-signal corresponding to each target frequency band independently, which can improve the accuracy of data alignment, so that subsequent processing based on the target to-be-classified physiological electric signal composed of the target to-be-classified sub-signals can be performed to help to improve the classification accuracy of the physiological electric signal.

Figure 5:
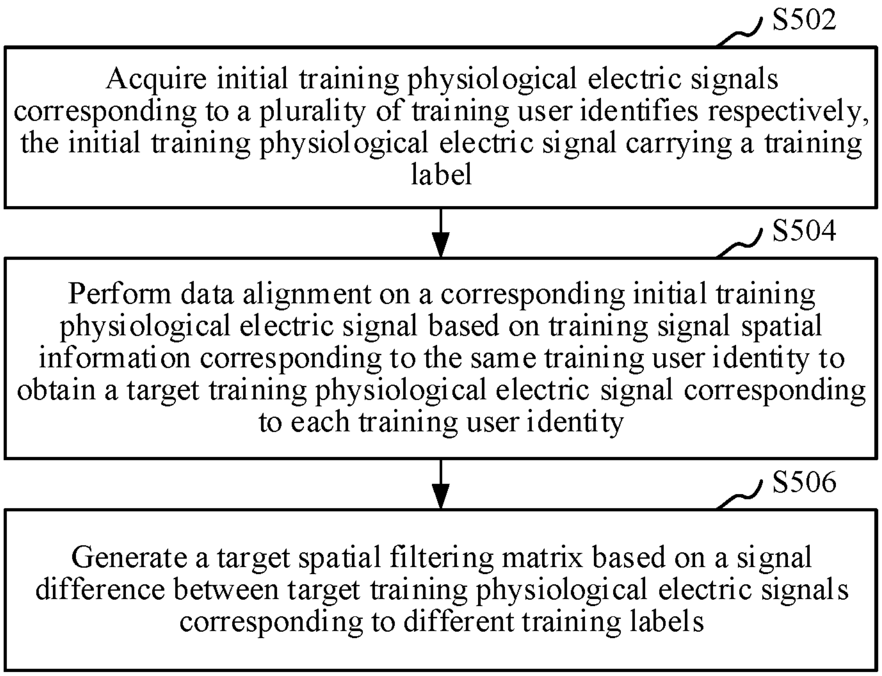
FIG. 5 is a schematic flowchart of generating a target spatial filtering matrix according to an embodiment.

In an embodiment, referring to FIG. 5, the generation of the target spatial filtering matrix includes the following steps:

Step S502: Acquire initial training physiological electric signals corresponding to a plurality of training user identifies respectively. The initial training physiological electric signals carry training labels.

Step S504: Perform data alignment on a corresponding initial training physiological electric signal based on training signal spatial information corresponding to the same training user identity to obtain a target training physiological electric signal corresponding to each training user identity.

Step S506: Generate a target spatial filtering matrix based on a signal difference between target training physiological electric signals corresponding to different training labels.

Specifically, a target spatial filtering matrix applicable to all users can be generated based on physiological electric signals with classification results known corresponding to a plurality of training users. Firstly, the computer device needs to acquire initial training physiological electric signals corresponding to a plurality of training user identities respectively, and perform data alignment on the corresponding initial training physiological electric signal based on the training signal spatial information corresponding to the same training user identity to obtain a target training physiological electric signal corresponding to each training user identity. That is, data alignment is performed on each training user independently. Then, the computer device may generate a target spatial filtering matrix based on the signal difference between the target training physiological electric signals corresponding to different training labels. The target spatial filtering matrix can maximize the spatial feature difference between different types of physiological electric signals.

In an embodiment, when the classification task is a two-classification task, the computer device may generate a target spatial filtering matrix based on a signal difference between a target training physiological electric signal corresponding to a training label A and a target training physiological electric signal corresponding to a training label B. When the classification task is a multi-classification task, the computer device may firstly convert the multi-classification task into a two-classification task by adopting a one-to-many or many-to-many method, firstly generate a corresponding first target spatial filtering matrix based on the two-classification task, then subdivide the two-classification task to generate a corresponding second target spatial filtering matrix until it can no longer be subdivided, and finally obtain a plurality of target spatial filtering matrices. Converting a multi-classification task into a two-classification task by adopting a one-to-many method refers to selecting one category from all categories as one category and other categories as the other category. Converting a multi-classification task into a two-classification task by adopting a many-to-many method refers to selecting one part of categories from all categories as one category and the other part of categories as the other category.

For example, when the classification task is a three-classification task, the computer device may generate a first target spatial filtering matrix based on the signal difference between the target training physiological electric signal corresponding to the training label A and the target training physiological electric signals corresponding to other training labels (training label B and training label C). The spatial feature obtained by performing spatial feature extraction on the physiological electric signal based on the first target spatial filtering matrix can be used for distinguishing whether the category of the physiological electric signal is the training label A. The computer device may generate a second target spatial filtering matrix based on the signal difference between the target training physiological electric signal corresponding to the training label B and the target training physiological electric signal corresponding to the training label C. The spatial feature obtained by performing spatial feature extraction on the physiological electric signal based on the second target spatial filtering matrix can be used for distinguishing whether the category of the physiological electric signal is the training label B or training label C. During specific application, spatial feature extraction is firstly performed on the to-be-classified physiological electric signal based on the first target spatial filtering matrix to obtain a first to-be-classified spatial feature. If the classification result corresponding to the to-be-classified physiological electric signal obtained based on the first to-be-classified spatial feature is the training label A, then the classification result corresponding to the to-be-classified physiological electric signal is the category corresponding to the training label A. If the classification result corresponding to the to-be-classified physiological electric signal obtained based on the first to-be-classified spatial feature is not the training label A, then spatial feature extraction is performed on the to-be-classified physiological electric signal based on the second target spatial filtering matrix to obtain a second to-be-classified spatial feature. Finally, whether the classification result corresponding to the to-be-classified physiological electric signal is the training label B or training label C is determined based on the second to-be-classified spatial feature.

In this embodiment, the distribution difference of the training samples between different training users can be reduced through data alignment, and then a target spatial filtering matrix that maximizing the spatial feature difference between different categories of physiological electric signals can be generated based on the signal difference between the target training physiological electric signals corresponding to different training labels, so that the physiological electric signal can be classified based on the to-be-classified spatial feature extracted from the target spatial filtering matrix.

In an embodiment, before performing data alignment on a corresponding initial training physiological electric signal based on training signal spatial information corresponding to the same training user identity to obtain a target training physiological electric signal corresponding to each training user identity, the method further includes:

generating a corresponding initial reference matrix based on each initial training physiological electric signal corresponding to the same training user identity to obtain the initial reference matrix corresponding to each training user identity; and using the initial reference matrix corresponding to the same training user identity as the corresponding training signal spatial information.

Specifically, before data alignment is performed, it is necessary to independently calculate the training signal spatial information corresponding to each training user. The computer device may generate a corresponding initial reference matrix based on each initial training physiological electric signal corresponding to the same training user identity to obtain the initial reference matrix corresponding to each training user identity, and then use the initial reference matrix corresponding to the same training user identity as the corresponding training signal spatial information. For example, the computer device generates an initial reference matrix a corresponding to a training user A based on each initial training physiological electric signal corresponding to the training user A, uses the initial reference matrix a as the training signal spatial information corresponding to the training user A, generates an initial reference matrix b corresponding to a training user B based on each initial training physiological electric signal corresponding to the training user B, and uses the initial reference matrix b as the training signal spatial information corresponding to the training user B.

In an embodiment, the initial reference matrix may be calculated by adopting the following formula:

$$R = \frac{1}{m}\sum_{i=1}^{m} x_i x_i^T$$

where R represents an initial reference matrix corresponding to a training user identity, m represents a total number of initial training physiological electric signals corresponding to a training user identity, $x_i$ represents the ith initial training physiological electric signal, $$x_i^T$$

represents the transposition of $x_i$, and $$x_i x_i^T$$

represents the covariance matrix corresponding to the ith initial training physiological electric signal. The initial reference matrix may be a mean value of the covariance matrix of all training samples of a training user.

In this embodiment, a corresponding initial reference matrix is generated based on each initial training physiological electric signal corresponding to the same training user identity to obtain the initial reference matrix corresponding to each training user identity, and the initial reference matrix corresponding to the same training user identity is used as the corresponding training signal spatial information. In this way, the reference matrix used for data alignment uses the relevant information of a large number of physiological electric signals of the same user, which can more accurately reflect the overall distribution situation of a plurality of physiological electric signals of a user.

In an embodiment, the initial training physiological electric signal includes an initial training sub-signals corresponding to at least one target frequency band respectively, and generating a corresponding initial reference matrix based on each initial training physiological electric signal corresponding to the same training user identity to obtain the initial reference matrix corresponding to each training user identity includes:

calculating an initial covariance matrix corresponding to each initial training sub-signal; calculating a corresponding initial reference sub-matrix based on each initial covariance matrix corresponding to the same training user identity and the same target frequency band to obtain the initial reference sub-matrix corresponding to each training user identity at each target frequency band; and obtaining the initial reference matrix corresponding to each training user identity based on each initial reference sub-matrix.

Specifically, when the reference matrix is calculated, calculation is performed independently for each target frequency band of each subject. The computer device may perform band-pass filtering on the training physiological electric signal, and obtain the initial training physiological electric signal composed of the initial training sub-signals corresponding to at least one target frequency band respectively based on the band-pass filtering result. Further, when the initial reference matrix is generated, the computer device firstly calculates the initial covariance matrix corresponding to each initial training sub-signal, and then calculates the corresponding initial reference sub-matrix based on each initial covariance matrix corresponding to the same training user identity and the same target frequency band to obtain the initial reference sub-matrix corresponding to each training user identity at each target frequency band. Then, the initial reference sub-matrices form the initial reference matrix corresponding to each training user identity. An initial reference sub-matrix may be a mean value of the covariance matrix of all training samples of a training user at a target frequency band. Accordingly, an initial reference matrix may be a combination of the mean values of the covariance matrices of all training samples of a training user at each target frequency band.

In this embodiment, when the reference matrix is calculated, calculation is performed independently for each target frequency band of each subject, which can improve the accuracy of the reference matrix, thus helping to improve the classification accuracy of the subsequent physiological electric signal.

In an embodiment, the initial training physiological electric signal includes channel signals corresponding to a plurality of acquisition channels on a physiological electric signal acquisition device, and the initial training sub-signal includes a channel sub-signal corresponding to each acquisition channel. Calculating an initial covariance matrix corresponding to each initial training sub-signal includes:

calculating a covariance between the channel sub-signals in a current initial training sub-signal; and generating an initial covariance matrix corresponding to the current initial training sub-signal based on the covariance between the channel sub-signals.

The physiological electric signal acquisition device is a device used for acquiring the physiological electric signal. The physiological electric signal acquisition device includes a plurality of electrodes, and different electrodes are used for acquiring electric signals at different positions. One electrode corresponds to one acquisition channel. The physiological electric signal is a multi-channel signal, including channel signals corresponding to each acquisition channel. The initial training sub-signal include channel sub-signals corresponding to each acquisition channel.

Specifically, the physiological electric signal is a multi-channel signal. The initial training physiological electric signal includes channel signals corresponding to a plurality of acquisition channels on the physiological electric signal acquisition device. The initial covariance matrix corresponding to the initial training physiological electric signal is a matrix composed of the covariance between the channel signals. In the current initial training sub-signal, the covariance between the channel sub-signals is calculated, and then the covariance between the channel sub-signals forms the initial covariance matrix corresponding to the current initial training sub-signal. By analogy, an initial covariance matrix corresponding to each initial training sub-signal can be obtained finally.

Figure 6:
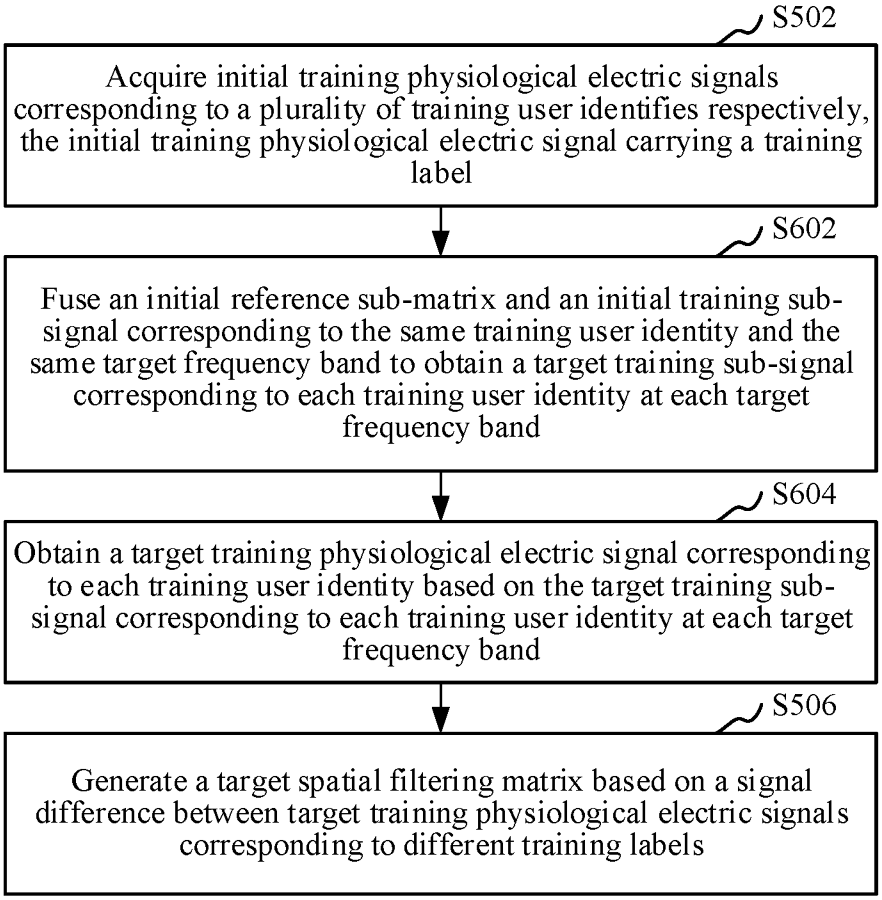
FIG. 6 is a schematic flowchart of generating a target spatial filtering matrix according to another embodiment.

In an embodiment, referring to FIG. 6, the initial reference matrix includes initial reference sub-matrices corresponding to at least one target frequency band respectively, and the initial training physiological electric signal includes initial training sub-signals corresponding to the at least one target frequency band respectively. Performing data alignment on each initial training physiological electric signal based on training signal spatial information corresponding to the same training user identity to obtain a target training physiological electric signal corresponding to each training user identity includes the following steps:

Step S602: Fuse the initial reference sub-matrix and the initial training sub-signal corresponding to the same training user identity and the same target frequency band to obtain a target training sub-signal corresponding to each training user identity at each target frequency band.

Step S604: Obtain the target training physiological electric signal corresponding to each training user identity based on the target training sub-signal corresponding to each training user identity at each target frequency band.

Specifically, during data alignment, it is performed independently for each target frequency band of each training user. If no band-pass filtering is performed on the physiological electric signal in the training process, the initial reference matrix and the initial training physiological electric signal corresponding to the same training user identity may be directly fused, so that data alignment is performed on the initial training physiological electric signal based on the initial reference matrix to obtain a target training physiological electric signal. If band-pass filtering has been performed on the physiological electric signal in the training process, each target frequency band of each training user requires independent data alignment when data alignment is performed. If band-pass filtering has been performed on the physiological electric signal, then the initial reference matrix includes initial reference sub-matrices corresponding to at least one target frequency band respectively, the initial training physiological electric signal includes initial training sub-signals corresponding to at least one target frequency band respectively, and the computer device may fuse the initial reference sub-matrix and the initial training sub-signal corresponding to the same training user identity and the same target frequency band to obtain a target training sub-signal corresponding to each training user identity at each target frequency band. Then, all target training sub-signals corresponding to the same training user identity are combined to obtain the corresponding target training physiological electric signal. Finally, the target training physiological electric signal corresponding to each training user identity can be obtained.

In this embodiment, when data alignment is performed, data alignment is performed independently for each target frequency band of each training user, which can improve the accuracy of data alignment, thus helping to improve the classification accuracy of the subsequent physiological electric signal.

Figure 7:
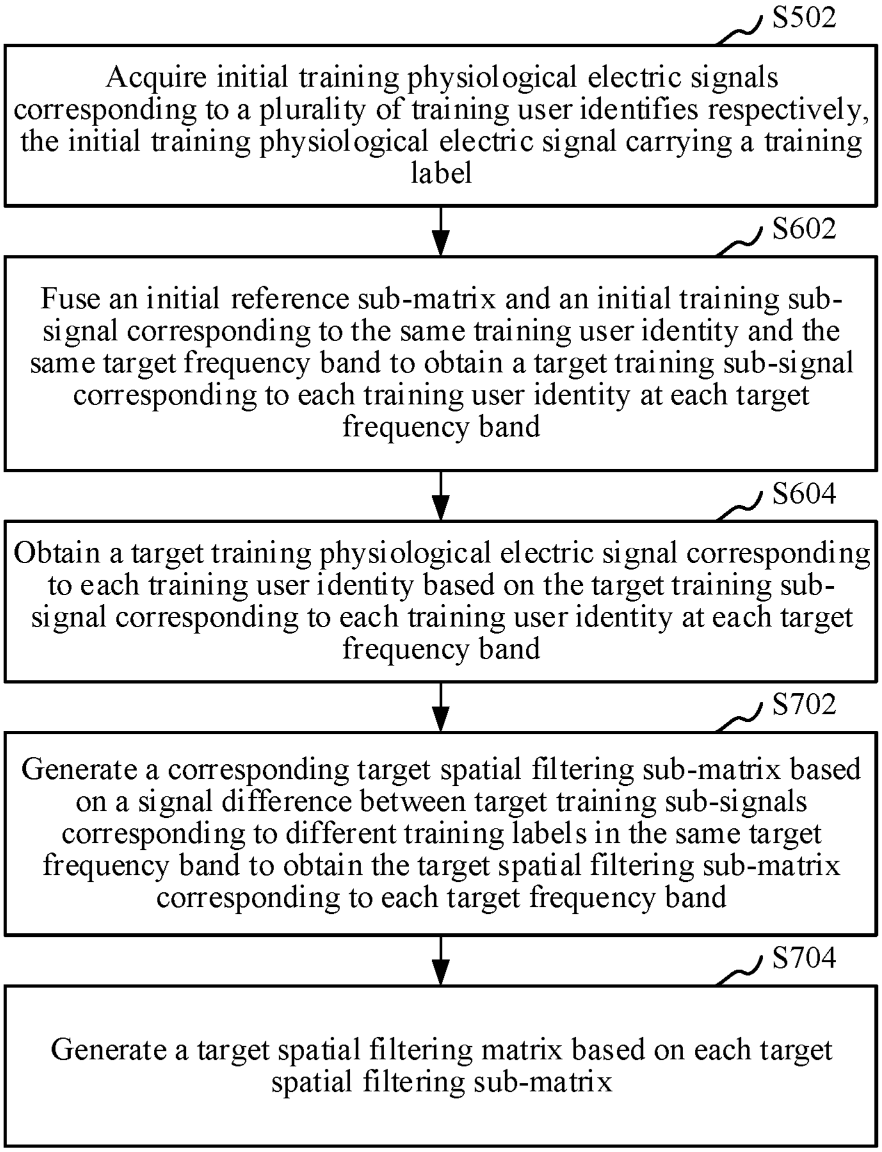
FIG. 7 is a schematic flowchart of generating a target spatial filtering matrix according to yet another embodiment.

In an embodiment, as shown in FIG. 7, the target training physiological electric signal includes a target training sub-signals corresponding to at least one target frequency band respectively, and generating the target spatial filtering matrix based on a signal difference between the target training physiological electric signals corresponding to different training labels includes the following steps:

Step S702: Generate a corresponding target spatial filtering sub-matrix based on a signal difference between target training sub-signals corresponding to different training labels in the same target frequency band to obtain the target spatial filtering sub-matrix corresponding to each target frequency band.

Step S704: Generate the target spatial filtering matrix based on each target spatial filtering sub-matrix.

Specifically, a corresponding spatial filter may be generated for each target frequency band. The computer device may generate a corresponding target spatial filtering sub-matrix based on a signal difference between target training sub-signals corresponding to different training labels in the same target frequency band to obtain the target spatial filtering sub-matrix corresponding to each target frequency band, and then all target spatial filtering sub-matrices form the target spatial filtering matrix.

For example, the target frequency band includes a frequency band 1, a frequency band 2 and a frequency band 3. Each target training physiological electric signal includes target training sub-signals corresponding to the frequency band 1, the frequency band 2 and the frequency band 3 respectively. In each target training sub-signal corresponding to the frequency band 1, a target spatial filtering sub-matrix corresponding to the frequency band 1 is generated based on a signal difference between the target training sub-signal corresponding to the training label A and the target training sub-signal corresponding to the training label B. In each target training sub-signal corresponding to the frequency band 2, a target spatial filtering sub-matrix corresponding to the frequency band 2 is generated based on a signal difference between the target training sub-signal corresponding to the training label A and the target training sub-signal corresponding to the training label B. In each target training sub-signal corresponding to the frequency band 3, a target spatial filtering sub-matrix corresponding to the frequency band 3 is generated based on a signal difference between the target training sub-signal corresponding to the training label A and the target training sub-signal corresponding to the training label B. Finally, the target spatial filtering sub-matrices corresponding to the frequency band 1, the frequency band 2 and the frequency band 3 respectively form the target spatial filtering matrix.

In this embodiment, the corresponding target spatial filtering sub-matrix is generated independently for each target frequency band, and the target spatial filtering sub-matrices form the target spatial filtering matrix. Then, in application, spatial feature extraction can be performed by frequency bands to improve the accuracy of feature extraction, thus improving the classification accuracy of the physiological electric signal.

In an embodiment, generating a corresponding target spatial filtering sub-matrix based on a signal difference between target training sub-signals corresponding to different training labels in the same target frequency band to obtain the target spatial filtering sub-matrix corresponding to each target frequency band includes:

calculating a target covariance matrix corresponding to each target training sub-signal in a current target frequency band; calculating a corresponding target reference matrix based on each target covariance matrix corresponding to the same training label to obtain the target reference matrix corresponding to each training label; fusing all target reference matrices to obtain a fused reference matrix, and performing eigenvalue decomposition on the fused reference matrix to obtain an initial eigenvalue matrix and an initial eigenvector matrix corresponding to the fused reference matrix; obtaining a whitening matrix based on the initial eigenvalue matrix and the initial eigenvector matrix; performing whitening transformation on each target reference matrix based on the whitening matrix to obtain a transformed reference matrix corresponding to each target reference matrix; performing eigenvalue decomposition on any one transformed reference matrix to obtain an eigenvalue decomposition result, and obtaining a target eigenvector matrix based on the eigenvalue decomposition result; and generating a target spatial filtering sub-matrix corresponding to the current target frequency band based on the whitening matrix and the target eigenvector matrix.

Eigenvalue decomposition refers to decomposing the matrix in eigenvector space and decomposing it into a plurality of eigenvectors. Each eigenvector can be understood as a direction, and an eigenvalue corresponding to the eigenvector is a projection of the matrix in that direction. Moreover, the eigenvector corresponding to the larger eigenvalue plays a leading role. Whitening transformation is used for removing redundant information of input data, which can reduce the correlation between features.

Specifically, the computer device can generate a spatial filter based on a common spatial pattern. In the current target frequency band, the computer device may firstly calculate a target covariance matrix corresponding to each target training sub-signal, and calculate a corresponding target reference matrix based on each target covariance matrix corresponding to the same training label to obtain the target reference matrix corresponding to each training label. When the target reference matrix is calculated, specifically the mean value of each target covariance matrix corresponding to the training label A can be used as the target reference matrix corresponding to the training label A, and the mean value of each target covariance matrix corresponding to the training label B can be used as the target reference matrix corresponding to the training label B. Then, the computer device fuses all target reference matrices to obtain a fused reference matrix, and performs eigenvalue decomposition on the fused reference matrix to obtain an initial eigenvalue matrix and an initial eigenvector matrix corresponding to the fused reference matrix. When all target reference matrices are fused, specifically all target reference matrices may be added to obtain the fused reference matrix. Then, the computer device obtains a whitening matrix based on the initial eigenvalue matrix and the initial eigenvector matrix, and performs whitening transformation on each target reference matrix based on the whitening matrix to obtain a transformed reference matrix corresponding to each target reference matrix. Since performing eigenvalue decomposition on each transformed reference matrix can obtain an eigenvalue decomposition result including corresponding data, the computer device may perform eigenvalue decomposition on any one transformed reference matrix to obtain an eigenvalue decomposition result, and obtain a target eigenvector matrix based on the eigenvalue decomposition result. Finally, the computer device may generate a target spatial filtering sub-matrix corresponding to the current target frequency band based on the whitening matrix and the target eigenvector matrix. Specifically, the whitening matrix and the target feature vector matrix may be fused, and the fused matrix is directly used as the target spatial filtering sub-matrix corresponding to the current target frequency band, or part of the data of the fused matrix may be extracted as the target spatial filtering sub-matrix corresponding to the current target frequency band.

In an embodiment, the target spatial filtering sub-matrix may be calculated by adopting the following formula. A two-classification task will be taken as an example to describe the generation process of the target spatial filtering sub-matrix corresponding to the current target frequency band.

1. Average covariance matrices $\overline{R_1}$ and $\overline{R_2}$ of two types of signals are calculated respectively, $$\overline{R_1} = \frac{1}{M*m}\sum_{i=1}^{M*m}\frac{X_i^1(X_i^1)^T}{\mathrm{trace}(X_i^1(X_i^1)^T)}$$

$$\overline{R_2} = \frac{1}{M*m}\sum_{i=1}^{M*m}\frac{X_i^2(X_i^2)^T}{\mathrm{trace}(X_i^2(X_i^2)^T)}$$

where $\overline{R_1}$ represents the average covariance matrix corresponding to a training label 1 (i.e., the target reference matrix corresponding to the training label 1), and $\overline{R_2}$ represents the average covariance matrix corresponding to a training label 2 (i.e., the target reference matrix corresponding to the training label 2); M represents the number of training user identities, that is, the number of training users, and m represents the number of target training physiological electric signals corresponding to each training user identity, that is, the number of training samples corresponding to each training user;

$$X_i^1$$

represents the ith target training sub-signal, the training label of this target training sub-signal is 1, $$X_i^1(X_i^1)^T$$

represents the target covariance matrix corresponding to the ith target training sub-signal, and the training label of this target training sub-signal is 1; trace (Y) represents the trace of the matrix Y, that is, the sum of diagonal elements of the matrix Y;

$$X_i^2$$

represents the ith target training sub-signal, the training label of this target training sub-signal is 2, $$X_i^2(X_i^2)^T$$

represents the target covariance matrix corresponding to the ith target training sub-signal, and the training label of this target training sub-signal is 2.

2. A composite covariance matrix R is calculated and eigenvalue decomposition is performed on the composite covariance matrix R, $$R=\overline{R_1}+\overline{R_2}=U\lambda U^T$$

where R represents the fused reference matrix, U represents the eigenvector matrix corresponding to the matrix R (i.e., the initial eigenvector matrix corresponding to the fused reference matrix), λ represents the eigenvalue matrix corresponding to the matrix R (i.e., the initial eigenvalue matrix corresponding to the fused reference matrix), λ is a diagonal matrix composed of the eigenvalues corresponding to each eigenvector in the eigenvector matrix, and $U^T$ represents the transposition of the matrix U.

3. A whitening matrix P is calculated, $$P=\sqrt{\lambda'^{-1}}\,U'^T$$

where λ' represents the eigenvalues matrix obtained by descending arrangement of eigenvalues, that is, the rearranged λ, and U' represents the eigenvector matrix corresponding to λ', that is, the rearranged U.

4. Whitening transformation and eigenvalue decomposition are performed on the average covariance matrices $\overline{R_1}$ and $\overline{R_2}$, $$S_1=P\overline{R_1}P^T=B_1\lambda_1B_1^T$$

$$S_2=P\overline{R_2}P^T=B_2\lambda_2B_2^T$$

$$B_1=B_2=B$$

where $S_1$ represents performing whitening transformation on $\overline{R_1}$ to obtain a transformed reference matrix, and $S_2$ represents performing whitening transformation on $\overline{R_2}$ to obtain a transformed reference matrix; $P^T$ represents transposition of the matrix P; $B_1$ and $\lambda_1$ are the eigenvalue decomposition results of $S_1$, and $B_2$ and $\lambda_2$ are the eigenvalue decomposition results of $S_2$; B is the target eigenvector matrix.

5. A spatial filter is calculated, that is, a target spatial filtering sub-matrix is calculated, $$W=B^TP$$

where W represents the target spatial filtering sub-matrix and $B^T$ represents the transposition of the matrix B.

In this embodiment, a spatial filter is generated based on a common spatial pattern. The spatial filter can maximize the variance between different categories of mapped samples, thus achieving the goal of classification and recognition.

In an embodiment, generating a target spatial filtering sub-matrix corresponding to the current target frequency band based on the whitening matrix and the target eigenvector matrix includes:

fusing the whitening matrix and the target eigenvector matrix to obtain an initial spatial filtering matrix; extracting at least one initial spatial filtering sub-matrix from the initial spatial filtering matrix to obtain at least one initial spatial filtering sub-matrix; and obtaining the target spatial filtering sub-matrix based on each initial spatial filtering sub-matrix.

Specifically, in order to reduce the amount of calculation, computer device may extract part of the data from the fused matrix of the whitening matrix and the target eigenvector matrix as the initial spatial filtering sub-matrix. The computer device firstly fuses the whitening matrix and the target eigenvector matrix to obtain the initial spatial filtering matrix, and extracts at least one initial spatial filtering sub-matrix from the initial spatial filtering matrix to obtain at least one initial spatial filtering sub-matrix. Then, all initial spatial filtering sub-matrix form a target spatial filtering sub-matrix. Specifically, one row of data of the initial spatial filtering matrix may be used as an initial spatial filtering sub-matrix, or several rows of data of the initial spatial filtering matrix may be used as an initial spatial filtering sub-matrix.

In an embodiment, the first two rows and the last two rows of a matrix W may be respectively selected as an initial spatial filtering sub-matrix, a certain row of the matrix W may be used as an initial spatial filtering sub-matrix to obtain four initial spatial filtering sub-matrices, and the four initial spatial filtering sub-matrices form a target spatial filtering sub-matrix. That is, a certain row of the matrix W is used as a spatial filter, and four spatial filters can be obtained by selecting the first two rows and the last two rows of the matrix W, and the four spatial filters form a spatial filter bank. The data in several first rows and the data in several last rows of the matrix W are quite different, and spatial features from different angles can be extracted from physiological electric signals.

In this embodiment, part of the data is extracted from the fused matrix of the whitening matrix and the target eigenvector matrix as the initial spatial filtering sub-matrix, and all initial spatial filtering sub-matrices form the target spatial filtering sub-matrix, thus reducing the amount of data in the target spatial filtering sub-matrix, reducing the subsequent calculation and improving the classification efficiency of the physiological electric signal.

In an embodiment, the target spatial filtering matrix includes target spatial filtering sub-matrices corresponding to at least one target frequency band respectively, and the target to-be-classified physiological electric signal includes target to-be-classified sub-signals corresponding to the at least one target frequency band respectively. Performing spatial feature extraction on the target to-be-classified physiological electric signal based on a target spatial filtering matrix to obtain a to-be-classified spatial feature includes:

extracting a spatial feature of a corresponding target to-be-classified sub-signal based on a target spatial filtering sub-matrix corresponding to the same target frequency band to obtain a to-be-classified spatial sub-feature corresponding to each target frequency band; and generating the to-be-classified spatial feature based on each to-be-classified spatial sub-feature.

Specifically, a spatial filter corresponding to each target frequency band can be generated based on the training samples, so spatial feature extraction is performed independently for each target frequency band when spatial feature extraction is performed. The target spatial filtering matrix includes target spatial filtering sub-matrices corresponding to at least one target frequency band respectively, and the target to-be-classified physiological electric signal includes target to-be-classified sub-signals corresponding to the at least one target frequency band respectively. The computer device may extract a spatial feature of a corresponding target to-be-classified sub-signal based on a target spatial filtering sub-matrix corresponding to the same target frequency band to obtain a to-be-classified spatial sub-feature corresponding to each target frequency band. Then, all to-be-classified spatial sub-features form a to-be-classified spatial feature. For example, spatial feature extraction is performed on a target to-be-classified sub-signal corresponding to a frequency band 1 based on a target spatial filtering sub-matrix corresponding to the frequency band 1 to obtain a to-be-classified spatial sub-feature 1, spatial feature extraction is performed on a target to-be-classified sub-signal corresponding to a frequency band 2 based on a target spatial filtering sub-matrix corresponding to the frequency band 2 to obtain a to-be-classified spatial sub-feature 2, and the to-be-classified spatial sub-feature 1 and the to-be-classified spatial sub-feature 2 are spliced to obtain a to-be-classified spatial feature.

In this embodiment, calculation is performed independently for each target frequency band when spatial feature extraction is performed, thus improving the accuracy and reliability of the to-be-classified spatial feature.

In an embodiment, the target spatial filtering sub-matrix includes at least one initial spatial filtering sub-matrix, and extracting a spatial feature of a corresponding target to-be-classified sub-signal based on a target spatial filtering sub-matrix corresponding to the same target frequency band to obtain a to-be-classified spatial sub-feature corresponding to each target frequency band includes:

performing signal projection on the corresponding target to-be-classified sub-signal based on each initial spatial filtering sub-matrix in a current target frequency band to obtain a target projection sub-signal corresponding to each target to-be-classified sub-signal; calculating initial variance data corresponding to each target projection sub-signal; performing normalization processing on the initial variance data to obtain corresponding target variance data; and obtaining the to-be-classified spatial sub-feature corresponding to the current target frequency band based on the target variance data.

Specifically, a spatial filter corresponding to a target frequency band may be a spatial filter bank. So, when spatial feature extraction is performed, it is necessary to perform spatial feature extraction on a physiological electric signal based on each spatial filter in the spatial filter bank, and obtain a to-be-classified spatial sub-feature based on each spatial feature extraction result. The computer device may perform signal projection on the corresponding target to-be-classified sub-signal based on each initial spatial filtering sub-matrix in a current target frequency band to obtain a target projection sub-signal corresponding to each target to-be-classified sub-signal. For example, the target spatial filtering sub-matrix corresponding to the current target frequency band includes four initial spatial filtering sub-matrices, signal projection is performed on the target to-be-classified sub-signal corresponding to the current target frequency band based on an initial spatial filtering sub-matrix a to obtain a target projection sub-signal a, signal projection is performed on the target to-be-classified sub-signal corresponding to the current target frequency band based on an initial spatial filtering sub-matrix b to obtain a target projection sub-signal b, signal projection is performed on the target to-be-classified sub-signal corresponding to the current target frequency band based on an initial spatial filtering sub-matrix c to obtain a target projection sub-signal c, and signal projection is performed on the target to-be-classified sub-signal corresponding to the current target frequency band based on an initial spatial filtering sub-matrix d to obtain a target projection sub-signal d. Then, the computer device calculates the initial variance data corresponding to each target projection sub-signal, performs normalization processing on the initial variance data to obtain the target variance data corresponding to the initial variance data, and finally splices all target variance data to obtain the to-be-classified spatial sub-feature corresponding to the current target frequency band.

In an embodiment, spatial feature extraction on a physiological electric signal based on a spatial filter bank in a target frequency band includes the following steps:

1. A sample projection is calculated, $$Z = W_f X$$

where Z represents the sample projection result, X represents the training sample and $W_f$ represents the spatial filter. For example, when X is the target to-be-classified sub-signal, $W_f$ is the initial spatial filtering sub-matrix, and Z is the target projection sub-signal.

2. A variance of the sample projection result corresponding to each spatial filter is calculated and normalization is performed, $$F = \frac{\mathrm{var}(Z)}{\mathrm{sum}(\mathrm{var}(Z))}$$

where F represents the normalized result of the variance, var(Z) represents the variance corresponding to Z, and sum(var(Z)) represents the sum of the variance.

3. All normalization results are spliced to obtain a spatial feature.

For example, assuming that a spatial filter bank corresponding to a target frequency band includes four spatial filters, for a sample A, four sample projection results Z1, Z2, Z3, and Z4 can be obtained through the four spatial filters, variance data corresponding to each sample projection result are calculated to obtain initial variance data V1, V2, V3, and V4, the four initial variances are added together to obtain variance statistics data, ratios of the four initial variances to the variance statistics data are calculated respectively to obtain sample features F1, F2, F3, F4, and the four sample features are spliced to finally obtain a to-be-classified spatial sub-feature corresponding to the target frequency band.

In this embodiment, the spatial filter can maximize the variance between different categories of mapped samples. Therefore, firstly sample projection is performed on the to-be-classified physiological electric signal, then the variance data are calculated and then normalization processing and splicing are performed. The to-be-classified spatial feature obtained based on the above processing can be used for classification and recognition to determine the classification result of the to-be-classified physiological electric signal.

In an embodiment, obtaining a classification result corresponding to the initial to-be-classified physiological electric signal based on the to-be-classified spatial feature includes:

inputting the to-be-classified spatial feature into a target physiological electric signal classification model to obtain the classification result.

The physiological electric signal classification model is a machine learning model used for classifying the physiological electric signal. The target physiological electric signal classification model refers to a trained physiological electric signal classification model.

Specifically, the computer device may perform classification processing on the to-be-classified spatial feature based on the machine learning model to obtain a classification result. The computer device may acquire the target physiological electric signal classification model, input the to-be-classified spatial feature into the target physiological electric signal classification model, and predict the classification result corresponding to the initial to-be-classified physiological electric signal through the target physiological electric signal classification model.

In this embodiment, by performing classification processing on the to-be-classified spatial feature based on the target physiological electric signal classification model, a more accurate classification result can be obtained quickly.

In an embodiment, a training process of the target physiological electric signal classification model includes:

performing spatial feature extraction on each target training physiological electric signal based on the target spatial filtering matrix to obtain a training spatial feature corresponding to each target training physiological electric signal; inputting each training spatial feature into an initial physiological electric signal classification model to obtain a prediction label corresponding to each target training physiological electric signal; and adjusting model parameters of the initial physiological electric signal classification model based on the prediction label and training label corresponding to the same target training physiological electric signal until a convergence condition is met to obtain the target physiological electric signal classification model.

The initial physiological electric signal classification model refers to a to-be-trained physiological electric signal classification model. The target physiological electric signal classification model refers to a trained physiological electric signal classification model.

Specifically, when the target physiological electric signal classification model is trained, the computer device may perform spatial feature extraction on each target training physiological electric signal based on the target spatial filtering matrix to obtain a training spatial feature corresponding to each target training physiological electric signal, use the training spatial feature corresponding to the target training physiological electric signal as the input of the model, use the training label corresponding to the target training physiological electric signal as the expected output of the model, and obtain the trained physiological electric signal classification model through supervised training. The computer device may specifically input the training spatial feature corresponding to the target training physiological electric signal into the initial physiological electric signal classification model to obtain a prediction label corresponding to the target training physiological electric signal, and adjust model parameters of the initial physiological electric signal classification model based on the prediction label and training label corresponding to the same target training physiological electric signal until a convergence condition is met to obtain the target physiological electric signal classification model. The convergence condition may be self-defined. For example, the number of iterations reaches an iteration threshold, or a difference between the training label and the prediction label reaches a minimum value. Adjusting the model parameters may specifically be to calculate the difference between the training label and the prediction label, adjust the model parameters of the initial physiological electric signal classification model through difference back propagation and continue the training until the updated difference or the number of iterations meet the convergence condition, so the training is completed and the trained physiological electric signal classification model is obtained. The target physiological electric signal classification model can be used for classifying the spatial feature corresponding to the to-be-classified physiological electric signal to obtain a classification result corresponding to the to-be-classified physiological electric signal.

In this embodiment, the target physiological electric signal classification model can be trained based on the training spatial feature and training label corresponding to each target training physiological electric signal, and the target physiological electric signal classification model can be used for performing classification processing on the target spatial feature corresponding to the to-be-classified physiological electric signal, thus improving the classification efficiency and classification accuracy of the physiological electric signal.

Figure 8:
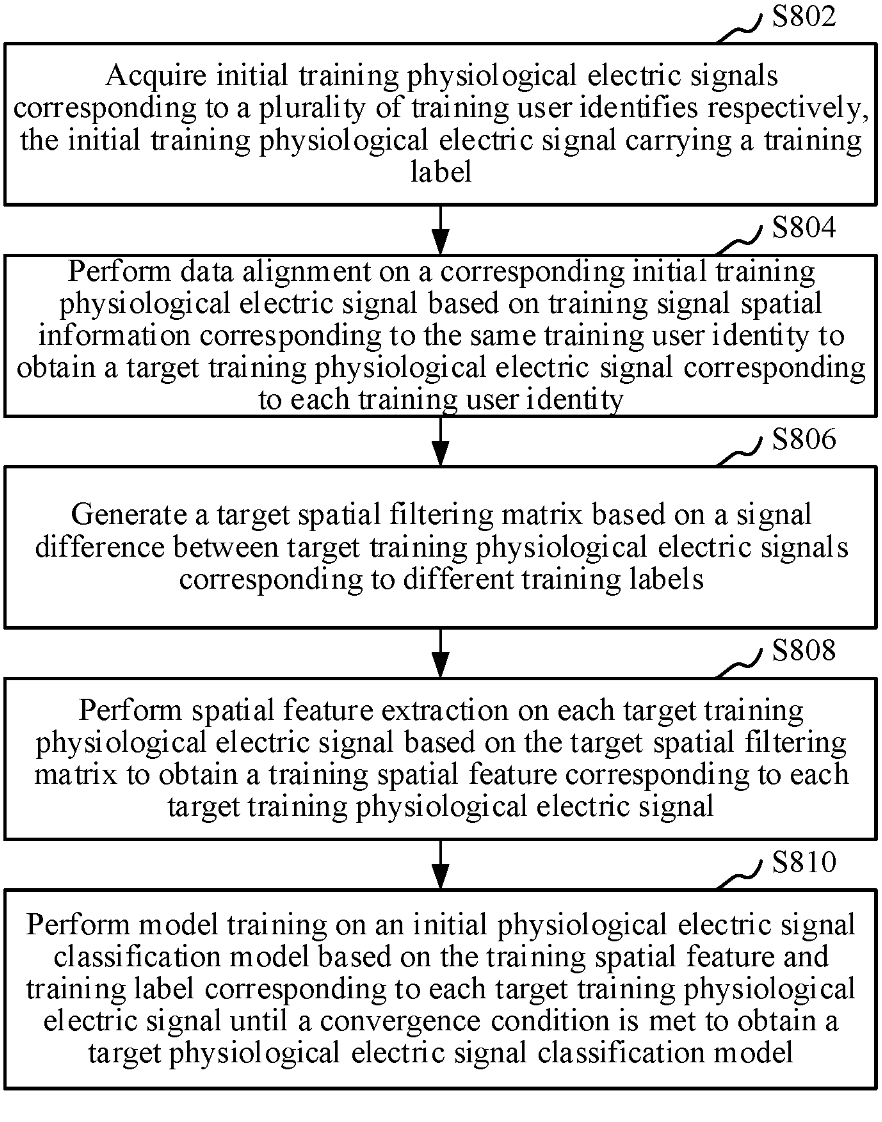
FIG. 8 is a schematic flowchart of a physiological electric signal classification processing method according to another embodiment.

In an embodiment, referring to FIG. 8, a physiological electric signal classification processing method is provided. Description will be made below by taking that the method is applied to a computer device in FIG. 1 as an example. The computer device may be the terminal 102 or the server 104 in FIG. 1. Referring to FIG. 8, the physiological electric signal classification processing method includes the following steps:

Step S802: Acquire initial training physiological electric signals corresponding to a plurality of training user identifies respectively. The initial training physiological electric signals carry training labels.

Specifically, the computer device may acquire training samples locally or from other terminals and servers to train a physiological electric signal classification model. The training samples are a plurality of initial training physiological electric signals corresponding to a plurality of training user identifies respectively. Each initial training physiological electric signal carries a corresponding training label.

Step S804: Perform data alignment on a corresponding initial training physiological electric signal based on training signal spatial information corresponding to the same training user identity to obtain a target training physiological electric signal corresponding to each training user identity.

Specifically, the computer device may generate a corresponding training signal spatial information based on each initial training physiological electric signal corresponding to the same training user identity to obtain the training signal spatial information corresponding to each training user identity. Then, the computer device may perform data alignment on the corresponding initial training physiological electric signal based on the training signal spatial information corresponding to the same training user identity to obtain a target training physiological electric signal corresponding to each training user identity. That is, data alignment is performed on each training user independently.

For the specific process of generating the signal spatial information and performing data alignment, a reference can be made to the method described in each relevant embodiment of the physiological electric signal classification processing method, which will not be repeated here.

Step S806: Generate a target spatial filtering matrix based on a signal difference between target training physiological electric signals corresponding to different training labels.

Specifically, the computer device may generate a target spatial filtering matrix based on the signal difference between the target training physiological electric signals corresponding to different training labels. The target spatial filtering matrix can maximize the spatial feature difference between different types of physiological electric signals.

For the specific process of generating the target spatial filtering matrix, a reference can be made to the method described in each relevant embodiment of the physiological electric signal classification processing method, which will not be repeated here.

Step S808: Perform spatial feature extraction on each target training physiological electric signal based on the target spatial filtering matrix to obtain a training spatial feature corresponding to each target training physiological electric signal.

Specifically, the computer device may perform spatial feature extraction on each target training physiological electric signal based on the target spatial filtering matrix to obtain a training spatial feature corresponding to each target training physiological electric signal, and perform training based on the training spatial features corresponding to different training labels to obtain a classifier, which is used for performing classification processing to the to-be-classified spatial feature corresponding to the to-be-classified physiological electric signal.

For the specific process of spatial feature extraction, a reference can be made to the method described in each relevant embodiment of the physiological electric signal classification processing method, which will not be repeated here.

Step S810: Perform model training on an initial physiological electric signal classification model based on the training spatial feature and training label corresponding to each target training physiological electric signal until a convergence condition is met to obtain a target physiological electric signal classification model.

Specifically, the computer device may use the training spatial feature as the input of the model, use the corresponding training label as the expected output, and obtain the trained physiological electric signal classification model through supervised training. The computer device may specifically input the training spatial feature corresponding to the target training physiological electric signal into the initial physiological electric signal classification model to obtain a prediction label corresponding to the target training physiological electric signal, and adjust model parameters of the initial physiological electric signal classification model based on the prediction label and training label corresponding to the same target training physiological electric signal until a convergence condition is met to obtain the target physiological electric signal classification model. The convergence condition may be self-defined. For example, the number of iterations reaches an iteration threshold, or a difference between the training label and the prediction label reaches a minimum value. Adjusting the model parameters may specifically be to calculate the difference between the training label and the prediction label, adjust the model parameters of the initial physiological electric signal classification model through difference back propagation and continue the training until the updated difference or the number of iterations meet the convergence condition, so the training is completed and the trained physiological electric signal classification model is obtained.

In application, the computer device may acquire the initial to-be-classified physiological electric signal corresponding to the target user identity, perform data alignment on the initial to-be-classified physiological electric signal based on the target signal spatial information corresponding to the target user identity to obtain the target to-be-classified physiological electric signal, perform spatial feature extraction on the target to-be-classified physiological electric signal based on the target spatial filtering matrix to obtain the to-be-classified spatial feature, and finally input the to-be-classified spatial feature into the target physiological electric signal classification model to obtain the classification result corresponding to the initial to-be-classified physiological electric signal.

For the specific application process of the target physiological electric signal classification model, a reference can be made to the method described in each relevant embodiment of the physiological electric signal classification processing method, which will not be repeated here.

In the physiological electric signal classification processing method, data alignment is performed on the corresponding initial physiological electric signal based on the training signal spatial information corresponding to the same training user identity, which can reduce the distribution difference between the physiological electric signals of different training users; and then a universal target spatial filtering matrix is generated based on the target physiological electric signal obtained through data alignment and the corresponding training label, the spatial feature in physiological electric signal that can be used for distinguishing the category of the physiological electric signal can be extracted through the target spatial filtering matrix, and then the extracted spatial feature is used as a training sample to train the universal physiological electric signal classification model. In this way, the target spatial filtering matrix and the target physiological electric signal classification model that can be used for classifying the physiological electric signal of the target user can be obtained through training without acquiring the physiological electric signal of the target user in advance. Through the target spatial filtering matrix and the target physiological electric signal classification model, the physiological electric signal of the target user can be classified, which is more convenient and efficient.

Figure 9A:
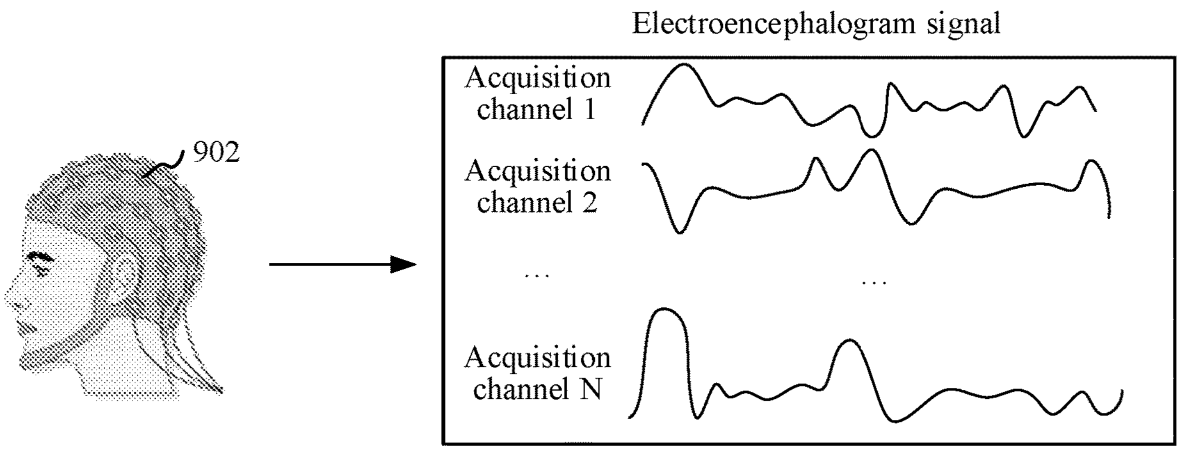
FIG. 9A is a schematic structural diagram of an EEG signal according to an embodiment.

The present disclosure further provides an application scenario in which the physiological electric signal classification processing method is applied. Specifically, the application of the physiological electric signal classification processing method in the present disclosure scenario is as follows:

The physiological electric signal classification processing method provided by the present disclosure can be applied to electroencephalogram signal classification tasks. Electroencephalogram (EEG) signals are physiological electric signals obtained from scalp electric signals amplified and recorded by an electronic instrument (i.e., acquisition device), which are multi-channel time series. Referring to FIG. 9A, the acquisition device includes a plurality of electrodes, one electrode corresponds to one acquisition channel, and a complete EEG signal is composed of EEG signals corresponding to a plurality of acquisition channels. 902 may represent an electrode.

Figure 9B:
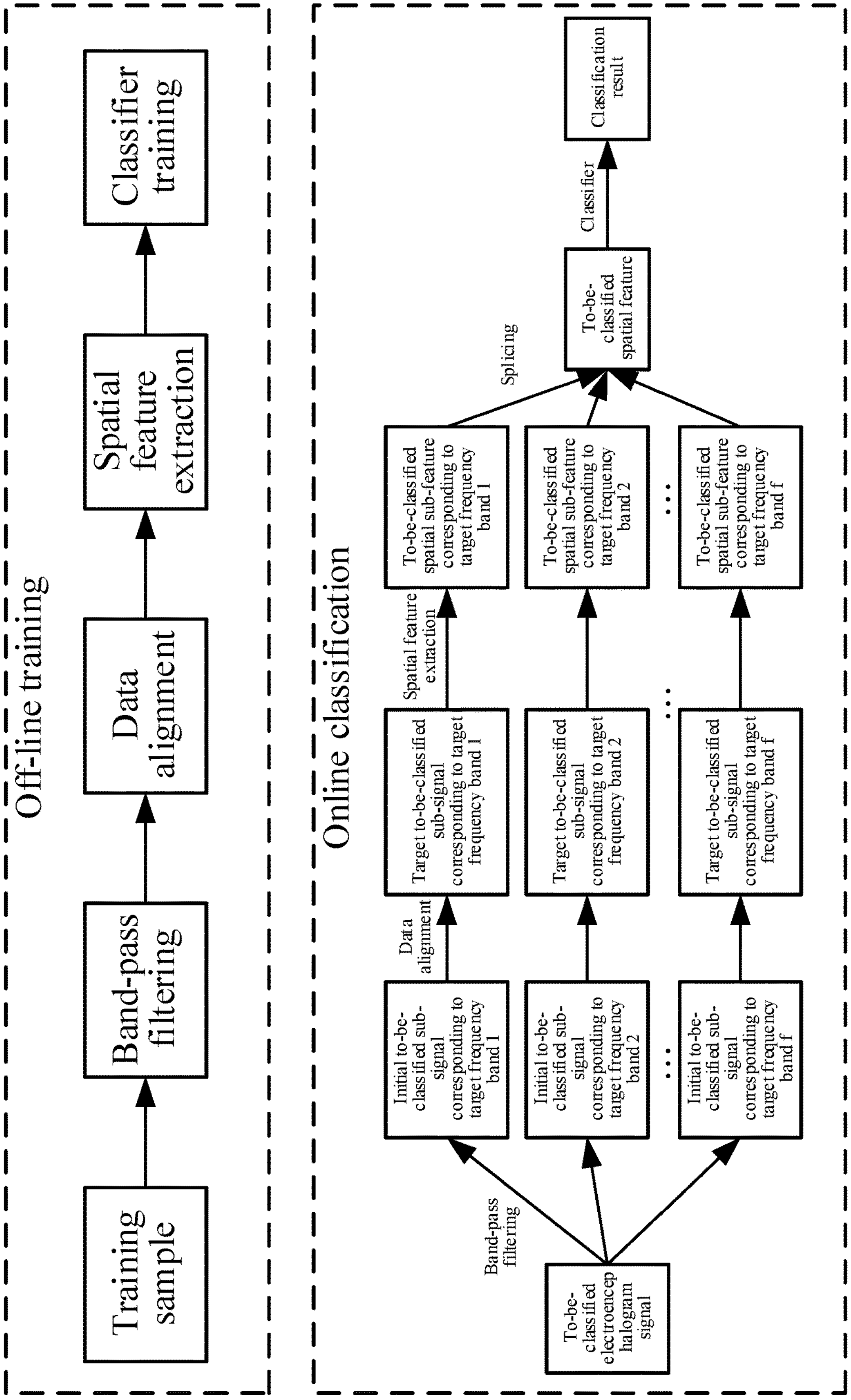
FIG. 9B is a schematic flowchart of EEG signal classification according to an embodiment.

The specific process of EEG signal classification will be described with reference to FIG. 9B.

1. Off-Line Training

Off-line training is mainly to train a robust classification model based on a large amount of data of different training users, so that it has high generalization for EEG signals of unknown users (i.e. target users). It is assumed that the training data are $$\{X^i\}_{i=1}^M,\ X^i \in R^{m*c*n},$$

where $X^i$ represents the training data of the ith training user, M represents the number of training users, m represents the number of training samples of each training user, c represents the number of acquisition channels of EEG signals, and n represents the number of sampling points of EEG signals.

1-1 Band-Pass Filtering

For all training data, the computer device firstly performs band-pass filtering on the original EEG training samples. The filtering frequency bands include a plurality of filtering frequency bands, and the frequency bands may or may not overlap. Then, the computer device can obtain EEG signals $$\left\{\{\text{X\_filtered}_j^i\}_{j=1}^N\right\}_{i=1}^M,\ \text{X\_filtered}_j^i \in R^{m*c*n}$$

at a plurality of target frequency bands, where N is the total number of filtering frequency bands, $$\text{X\_filtered}_j^i$$

represents the data of the EEG signal of the ith training user under the jth target frequency band.

1-2 Data Alignment

For the filtered training samples, data alignment is performed to reduce the difference of the training sample covariance matrix between different training users. Specifically, European distance alignment may be adopted. European distance alignment is a method based on reference matrix, and calculation is performed independently for each target frequency band of each training user. Let a specific frequency band sample of a certain training user be x, $x \in R^{m*c*n}$. Assuming that the reference matrix is R, for each training sample $x_i \in R^{c*n}$, data alignment may be performed by adopting the following formula:

$$\tilde{x}_r = R^{-\frac{1}{2}} x_i$$

The reference matrix R is the mean value of the covariance matrix of all training samples at each frequency band of each training user, which may be calculated by adopting the following formula:

$$R = \frac{1}{m}\sum_{i=1}^{m} x_i x_i^T$$

By European distance alignment, the average covariance matrix of all training users can be converted into a unit matrix, which is considered to reduce the distribution difference of the covariance matrix between different training users.

1-3 Spatial Feature Extraction

Through band-pass filtering and data alignment, the computer device can obtain training samples $$\{\{\tilde{X}_j^i\}_{j=1}^N\}_{i=1}^M$$

of each training user with similar covariance matrix distribution. where M is the total number of training users, and N is the total number of target frequency bands. Then, the computer device mixes all the aligned training samples, and extracts the spatial features of the training samples for each target frequency band by using a common spatial pattern. Common spatial pattern is a spatial feature extraction method based on covariance matrix, which aims to find an optimal spatial filter to maximize the variance between different categories of mapped samples, so as to achieve the goal of classification and recognition.

1-3-1 A Spatial Filter Band (i.e., Target Spatial Filtering Matrix) is Calculated.

(1) Average covariance matrices $\overline{R_1}$ and $\overline{R_2}$ of two types of signals are calculated respectively.

(2) A composite covariance matrix R is calculated and eigenvalue decomposition is performed on the composite covariance matrix R.

(3) A whitening matrix P is calculated.

(4) Whitening transformation and eigenvalue decomposition are performed on the average covariance matrices $\overline{R_1}$ and $\overline{R_2}$.

(5) A spatial filter bank is calculated, that is, a target spatial filtering sub-matrix is calculated.

1-3-2 Spatial Feature Extraction is Performed Based on the Spatial Filter Bank.

(1) Sample projections corresponding to the training samples after data alignment are calculated.

(2) A variance of the sample projection result corresponding to each spatial filter is calculated and normalization is performed.

(3) All normalization results are spliced to obtain a training spatial feature corresponding to each training sample.

1-4 Classifier Training

A logistic regression classifier is trained based on the training spatial feature and training label corresponding to each training sample.

2. Online Prediction

The spatial filter bank and logical regression classifier at each frequency band obtained through calculation based on off-line training can be applied to an online brain-computer interface system for signal recognition. However, in the online prediction process, a signal sample of an unknown user appears separately, and a reference matrix cannot be calculated. Therefore, the scheme of gradually modifying the reference matrix during system operation can be adopted to adapt to the data distribution of the unknown user.

2-1 Band-Pass Filtering

Firstly, the reference matrix $R_i=0$, i=1,2,3, . . . , F is initialized. At the beginning, the number of samples of the target user N=0, where F is the total number of target frequency bands.

Assuming that the to-be-classified EEG signal is $x \in R^{c*n}$, the computer device performs band-pass filtering on the to-be-classified EEG signal to obtain a filtered to-be-classified EEG signal $$\{x_i\}_{i=1}^{F} \in R^{c*n}.$$

That is, after band-pass filtering is performed on the to-be-classified EEG signal, an initial to-be-classified sub-signal corresponding to a target frequency band 1, an initial to-be-classified sub-signal corresponding to a target frequency band 2, an initial to-be-classified sub-signal corresponding to a target frequency band 3, . . . and an initial to-be-classified sub-signal corresponding to a target frequency band f can be obtained.

2-2 Data Alignment

Firstly, the reference matrix $$R_i = \frac{R_i * N + x_i x_i^T}{N+1}$$

and the number of samples of the target user N=N+1 are updated. Then, the updated reference matrix is used to perform Euclidean distance alignment on the filtered to-be-classified EEG signal:

$$\tilde{x}_i = R^{-\frac{1}{2}} x_i.$$

That is, after data alignment is performed on the to-be-classified EEG signal, a target to-be-classified sub-signal corresponding to the target frequency band 1, a target to-be-classified sub-signal corresponding to the target frequency band 2, a target to-be-classified sub-signal corresponding to the target frequency band 3, . . . and a target to-be-classified sub-signal corresponding to the target frequency band f can be obtained.

2-3 Spatial Feature Extraction

For the EEG signal at each target frequency band, the corresponding to-be-classified spatial sub-feature is extracted based on the trained spatial filter bank, and then the to-be-classified spatial sub-features at all target frequency bands are spliced to obtain a final to-be-classified spatial feature. That is, after spatial feature extraction is performed on the to-be-classified EEG signal, a to-be-classified spatial sub-feature corresponding to the target frequency band 1, a to-be-classified spatial sub-feature corresponding to the target frequency band 2, . . . and a to-be-classified spatial sub-feature corresponding to the target frequency band f can be obtained. The to-be-classified spatial sub-features corresponding to the target frequency bands 1, 2, . . . and f are spliced to obtain a to-be-classified spatial feature.

2-4 Feature Classification

Feature classification is performed by using the trained logistic regression classifier. The to-be-classified spatial feature is input into the trained classifier to obtain a classification result corresponding to the to-be-classified EEG signal.

Repeat steps 2-1 to 2-4 to classify each EEG signal of the target user online, so as to realize online classification of the EEG signals of unknown users.

In this embodiment, the distribution difference of EEG signals of different users can be reduced, thus realizing cross-user EEG signal classification. In addition, after offline training, the trained parameters can be embedded into the online brain-computer interface system, and the signal distribution can be adjusted adaptively with the acquisition of signal samples of unknown users, thus realizing the online classification of EEG signals of unknown users.

It is to be understood that in addition to being applied to the EEG signal classification tasks, the physiological electric signal classification processing method provided by the present disclosure can also be applied to other physiological electric signal classification tasks, such as electrocardiogram signal classification tasks and electromyogram signal classification tasks. For example, when a user is doing exercise, muscle state classification may be performed on the electromyogram signal of the user. When a muscle state indicates muscle fatigue, prompt information is generated to prompt the user to rest in time.

It is to be understood that, steps in flowcharts of FIG. 2 to FIG. 8 are displayed in sequence based on indication of arrows, but the steps are not necessarily performed in sequence based on a sequence indicated by the arrows. Unless otherwise explicitly specified in this specification, execution of the steps is not strictly limited, and the steps may be performed in other sequences. In addition, at least some steps in FIG. 2 to FIG. 8 may include a plurality of steps or a plurality of stages, and these steps or stages are not necessarily performed at a same time instant, but may be performed at different time instants. The steps or stages are not necessarily performed in sequence, but may be performed by turn or alternately with other steps or at least part of steps or stages in other steps.

Figure 10:
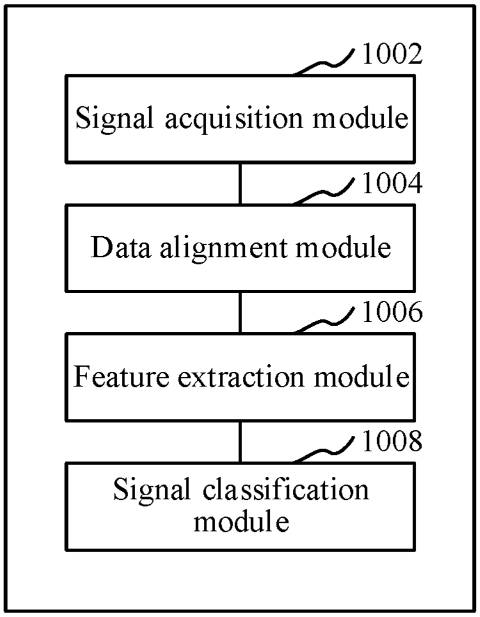
FIG. 10 is a structural block diagram of a physiological electric signal classification processing apparatus according to an embodiment.

In an embodiment, referring to FIG. 10, a physiological electric signal classification processing apparatus is provided. The apparatus can adopt software modules or hardware modules, or a combination of the two to become a part of the computer device. The apparatus specifically includes a signal acquisition module 1002, a data alignment module 1004, a feature extraction module 1006 and a signal classification module 1008.

The signal acquisition module 1002 is configured to acquire an initial to-be-classified physiological electric signal corresponding to a target user identity.

The data alignment module 1004 is configured to perform data alignment on the initial to-be-classified physiological electric signal based on target signal spatial information corresponding to the target user identify to obtain a target to-be-classified physiological electric signal.

The feature extraction module 1006 is configured to perform spatial feature extraction on the target to-be-classified physiological electric signal based on a target spatial filtering matrix to obtain a to-be-classified spatial feature. The target spatial filtering matrix is generated based on target training physiological electric signals corresponding to a plurality of training user identities respectively and training labels corresponding to the target training physiological electric signals. The target training physiological electric signals are obtained by performing data alignment on initial training physiological electric signals based on training signal spatial information corresponding to the training user identities.

The signal classification module 1008 is configured to obtain a classification result corresponding to the initial to-be-classified physiological electric signal based on the to-be-classified spatial feature.

In an embodiment, the signal acquisition module is further configured to acquire a candidate to-be-classified physiological electric signal corresponding to the target user identity; performing signal extraction of at least one target frequency band for the candidate to-be-classified physiological electric signal to obtain an initial to-be-classified sub-signal corresponding to the candidate to-be-classified physiological electric signal at each target frequency band; obtaining the initial to-be-classified physiological electric signal based on each initial to-be-classified sub-signal.

In an embodiment, the data alignment module is further configured to acquire an initial reference matrix corresponding to the initial to-be-classified physiological electric signal; modify the initial reference matrix based on the initial to-be-classified physiological electric signal to obtain a modified reference matrix corresponding to the initial to-be-classified physiological electric signal; and use the modified reference matrix corresponding to the initial to-be-classified physiological electric signal as the target signal spatial information.

In an embodiment, the initial reference matrix is a modified reference matrix corresponding to a previous to-be-classified physiological electric signal corresponding to the target user identity.

In an embodiment, the data alignment module is further configured to acquire a number statistics result of classified physiological electric signals corresponding to the target user identity; calculate a to-be-classified covariance matrix corresponding to the initial to-be-classified physiological electric signal; and modifying the initial reference matrix based on the number statistics result and the to-be-classified covariance matrix to obtain a modified reference matrix corresponding to the initial to-be-classified physiological electric signal.

In an embodiment, the initial reference matrix includes initial reference sub-matrices corresponding to at least one target frequency band respectively, and the initial to-be-classified physiological electric signal includes an initial to-be-classified sub-signal corresponding to the at least one target frequency band. The data alignment module is further configured to modify the corresponding initial reference sub-matrix based on the initial to-be-classified sub-signals corresponding to the same target frequency band and the number statistics result to obtain a modified reference sub-matrix corresponding to each target frequency band; and obtaining the modified reference matrix based on each modified reference sub-matrix.

In an embodiment, the modified reference matrix corresponding to the initial to-be-classified physiological electric signal includes modified reference sub-matrices corresponding to at least one target frequency band respectively, and the initial to-be-classified physiological electric signal includes initial to-be-classified sub-signals corresponding to the at least one target frequency band respectively. The data alignment module is further configured to fuse the modified reference sub-matrix and the initial to-be-classified sub-signal corresponding to the same target frequency band to obtain a target to-be-classified sub-signal corresponding to each target frequency band; and obtaining the target to-be-classified physiological electric signal based on each target to-be-classified sub-signal.

Figure 11:
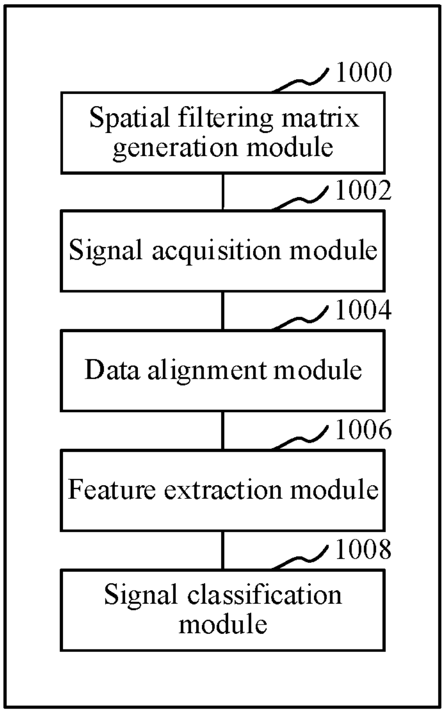
FIG. 11 is a structural block diagram of a physiological electric signal classification processing apparatus according to another embodiment.

In an embodiment, as shown in FIG. 11, the apparatus further includes:

a spatial filtering matrix generation module 1000, configured to acquire initial training physiological electric signals corresponding to a plurality of training user identifies respectively; the initial training physiological electric signals carrying training labels; perform data alignment on a corresponding initial training physiological electric signal based on training signal spatial information corresponding to the same training user identity to obtain a target training physiological electric signal corresponding to each training user identity; and generate the target spatial filtering matrix based on a signal difference between the target training physiological electric signals corresponding to different training labels.

In an embodiment, the spatial filtering matrix generation module is further configured to generate a corresponding initial reference matrix based on each initial training physiological electric signal corresponding to the same training user identity to obtain the initial reference matrix corresponding to each training user identity; and use the initial reference matrix corresponding to the same training user identity as the corresponding training signal spatial information.

In an embodiment, the initial training physiological electric signal includes initial training sub-signals corresponding to at least one target frequency band respectively. The spatial filtering matrix generation module is further configured to calculate an initial covariance matrix corresponding to each initial training sub-signal; calculate a corresponding initial reference sub-matrix based on each initial covariance matrix corresponding to the same training user identity and the same target frequency band to obtain the initial reference sub-matrix corresponding to each training user identity at each target frequency band; and obtain the initial reference matrix corresponding to each training user identity based on each initial reference sub-matrix.

In an embodiment, the initial training physiological electric signal includes channel signals corresponding to a plurality of acquisition channels on a physiological electric signal acquisition device, and the initial training sub-signal includes a channel sub-signal corresponding to each acquisition channel. The spatial filtering matrix generation module is further configured to calculate a covariance between the channel sub-signals in a current initial training sub-signal; and generate an initial covariance matrix corresponding to the current initial training sub-signal based on the covariance between the channel sub-signals.

In an embodiment, the initial reference matrix includes initial reference sub-matrices corresponding to at least one target frequency band respectively, and the initial training physiological electric signal includes initial training sub-signals corresponding to the at least one target frequency band respectively. The spatial filtering matrix generation module is further configured to fuse the initial reference sub-matrix and the initial training sub-signal corresponding to the same training user identity and the same target frequency band to obtain a target training sub-signal corresponding to each training user identity at each target frequency band; and obtain the target training physiological electric signal corresponding to each training user identity based on the target training sub-signal corresponding to each training user identity at each target frequency band.

In an embodiment, the target training physiological electric signal includes target training sub-signals corresponding to at least one target frequency band respectively. The spatial filtering matrix generation module is further configured to generate a corresponding target spatial filtering sub-matrix based on a signal difference between target training sub-signals corresponding to different training labels in the same target frequency band to obtain the target spatial filtering sub-matrix corresponding to each target frequency band; and generate the target spatial filtering matrix based on each target spatial filtering sub-matrix.

In an embodiment, the spatial filtering matrix generation module is further configured to calculate a target covariance matrix corresponding to each target training sub-signal in a current target frequency band; calculate a corresponding target reference matrix based on each target covariance matrix corresponding to the same training label to obtain the target reference matrix corresponding to each training label; fuse all target reference matrices to obtain a fused reference matrix, and perform eigenvalue decomposition on the fused reference matrix to obtain an initial eigenvalue matrix and an initial eigenvector matrix corresponding to the fused reference matrix; obtain a whitening matrix based on the initial eigenvalue matrix and the initial eigenvector matrix; perform whitening transformation on each target reference matrix based on the whitening matrix to obtain a transformed reference matrix corresponding to each target reference matrix; perform eigenvalue decomposition on any one transformed reference matrix to obtain an eigenvalue decomposition result, and obtain a target eigenvector matrix based on the eigenvalue decomposition result; and generate a target spatial filtering sub-matrix corresponding to the current target frequency band based on the whitening matrix and the target eigenvector matrix.

In an embodiment, the spatial filtering matrix generation module is further configured to fuse the whitening matrix and the target eigenvector matrix to obtain an initial spatial filtering matrix; extract at least one initial spatial filtering sub-matrix from the initial spatial filtering matrix to obtain at least one initial spatial filtering sub-matrix; and obtain the target spatial filtering sub-matrix based on each initial spatial filtering sub-matrix.

In an embodiment, the target spatial filtering matrix includes target spatial filtering sub-matrices corresponding to at least one target frequency band respectively, and the target to-be-classified physiological electric signal includes target to-be-classified sub-signals corresponding to the at least one target frequency band respectively. The feature extraction module is further configured to extract a spatial feature of a corresponding target to-be-classified sub-signal based on a target spatial filtering sub-matrix corresponding to the same target frequency band to obtain a to-be-classified spatial sub-feature corresponding to each target frequency band; and generate the to-be-classified spatial feature based on each to-be-classified spatial sub-feature.

In an embodiment, the target spatial filtering sub-matrix includes at least one initial spatial filtering sub-matrix. The feature extraction module is further configured to perform signal projection on the corresponding target to-be-classified sub-signal based on each initial spatial filtering sub-matrix in a current target frequency band to obtain a target projection sub-signal corresponding to each target to-be-classified sub-signal; calculate initial variance data corresponding to each target projection sub-signal; perform normalization processing on the initial variance data to obtain corresponding target variance data; and obtain the to-be-classified spatial sub-feature corresponding to the current target frequency band based on the target variance data.

In an embodiment, the signal classification module is further configured to input the to-be-classified spatial feature into a target physiological electric signal classification model to obtain the classification result.

Figure 12:
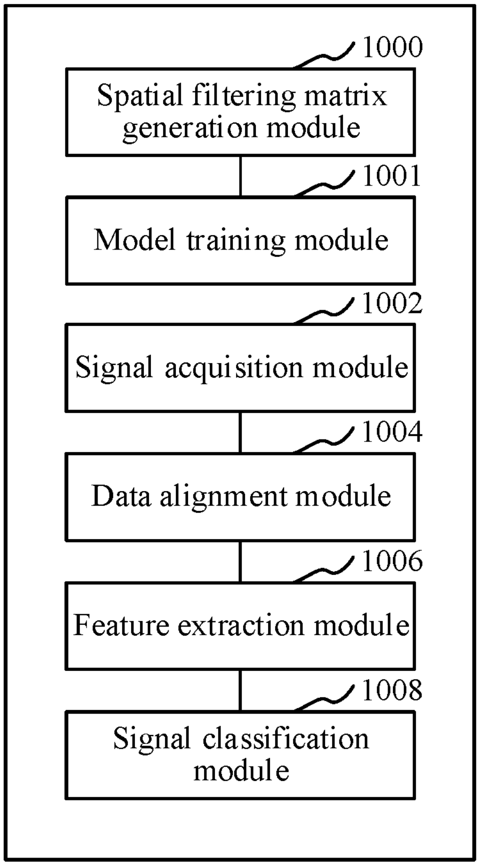
FIG. 12 is a structural block diagram of a physiological electric signal classification processing apparatus according to yet another embodiment.

In an embodiment, as shown in FIG. 12, the apparatus further includes:

a training feature extraction module 1001 configured to perform spatial feature extraction on each target training physiological electric signal based on the target spatial filtering matrix to obtain a training spatial feature corresponding to each target training physiological electric signal; input each training spatial feature into an initial physiological electric signal classification model to obtain a prediction label corresponding to each target training physiological electric signal; and adjust model parameters of the initial physiological electric signal classification model based on the prediction label and training label corresponding to the same target training physiological electric signal until a convergence condition is met to obtain the target physiological electric signal classification model.

In the physiological electric signal classification processing apparatus, firstly data alignment is performed on the corresponding initial physiological electric signal based on the training signal spatial information corresponding to the same training user identity, which can reduce the distribution difference between the physiological electric signals of different training users; and then a universal target spatial filtering matrix is generated based on the target physiological electric signal obtained through data alignment and the corresponding training label, and the spatial feature in physiological electric signal that can be used for distinguishing the category of the physiological electric signal can be extracted through the target spatial filtering matrix. Then, when classifying a physiological electric signal of an unknown user, firstly data alignment is performed on an initial to-be-classified physiological electric signal corresponding to a target user identity based on target signal spatial information corresponding to the target user identity, so as to reduce the distribution difference between the physiological electric signals of the target user and the training user, and then the spatial feature of the target to-be-classified physiological electric signal obtained by data alignment is extracted based on the universal target spatial filtering matrix, so that a classification result corresponding to the initial to-be-classified physiological electric signal can be obtained based on the extracted to-be-classified spatial feature. In this way, the physiological electric signal of the target user can be classified without acquiring it in advance, which is more convenient and efficient.

Figure 13:
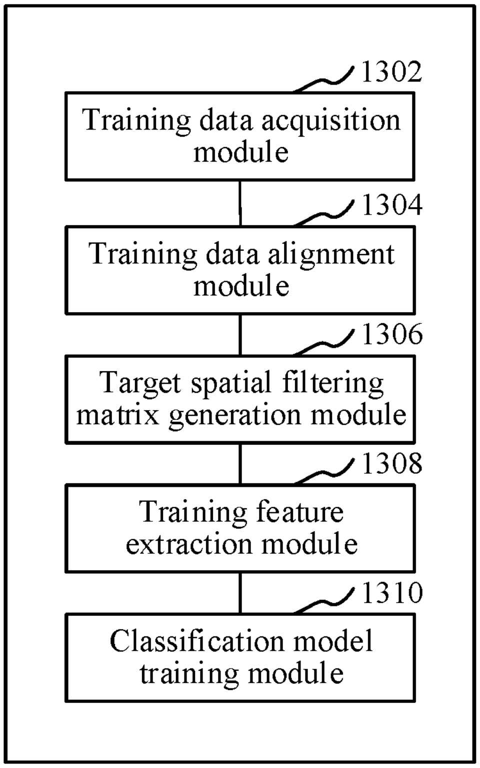
FIG. 13 is a structural block diagram of a physiological electric signal classification processing apparatus according to yet another embodiment.

In an embodiment, referring to FIG. 13, a physiological electric signal classification processing apparatus is provided. The apparatus can adopt software modules or hardware modules, or a combination of the two to become a part of the computer device. The apparatus specifically includes a training data acquisition module 1302, a training data alignment module 1304, a target spatial filtering matrix generation module 1306, a training feature extraction module 1308 and a classification model training module 1310.

The training data acquisition module 1302 is configured to acquire initial training physiological electric signals corresponding to a plurality of training user identifies respectively. The initial training physiological electric signals carry training labels.

The training data alignment module 1304 is configured to perform data alignment on a corresponding initial training physiological electric signal based on training signal spatial information corresponding to the same training user identity to obtain a target training physiological electric signal corresponding to each training user identity.

The target spatial filtering matrix generation module 1306 is configured to generate a target spatial filtering matrix based on a signal difference between target training physiological electric signals corresponding to different training labels.

The training feature extraction module 1308 is configured to perform spatial feature extraction on each target training physiological electric signal based on the target spatial filtering matrix to obtain a training spatial feature corresponding to each target training physiological electric signal.

The classification model training module 1310 is configured to perform model training on an initial physiological electric signal classification model based on the training spatial feature and training label corresponding to each target training physiological electric signal until a convergence condition is met to obtain a target physiological electric signal classification model.

In the physiological electric signal classification processing apparatus, data alignment is performed on the corresponding initial physiological electric signal based on the training signal spatial information corresponding to the same training user identity, which can reduce the distribution difference between the physiological electric signals of different training users; and then a universal target spatial filtering matrix is generated based on the target physiological electric signal obtained through data alignment and the corresponding training label, the spatial feature in physiological electric signal that can be used for distinguishing the category of the physiological electric signal can be extracted through the target spatial filtering matrix, and then the extracted spatial feature is used as a training sample to train the universal physiological electric signal classification model. In this way, the target spatial filtering matrix and the target physiological electric signal classification model that can be used for classifying the physiological electric signal of the target user can be obtained through training without acquiring the physiological electric signal of the target user in advance. Through the target spatial filtering matrix and the target physiological electric signal classification model, the physiological electric signal of the target user can be classified, which is more convenient and efficient.

For the specific definition of the physiological electric signal classification processing apparatus, a reference can be made to the definition of the physiological electric signal classification processing method above, which will not be repeated here. The modules in the foregoing physiological electric signal classification processing apparatus may be implemented entirely or partially by software, hardware, or a combination thereof. The foregoing modules may be built in or independent of a processor of a computer device in a hardware form, or may be stored in a memory of the computer device in a software form, so that the processor invokes and performs an operation corresponding to each of the foregoing modules.

In an embodiment, a computer device is provided. The computer device may be a server, and an internal structure diagram thereof may be shown in FIG. 14. The computer device includes a processor, a memory, and a network interface that are connected by using a system bus. The processor of the computer device is configured to provide computing and control capabilities. The memory of the computer device includes a non-volatile storage medium and an internal memory. The non-volatile storage medium stores an operating system, computer-readable instructions, and a database. The internal memory provides an environment for running of the operating system and the computer-readable instruction in the non-volatile storage medium. The database of the computer device is used for storing the target spatial filtering matrix, target signal spatial information, target physiological electric signal classification model data. The network interface of the computer device is configured to communicate with an external terminal through a network connection. The computer-readable instruction is executed by the processor to implement a method for classification processing of an electrophysiological signal.

In an embodiment, a computer device is provided. The computer device may be a terminal, and an internal structure diagram thereof may be shown in FIG. 15. The computer device includes a processor, a memory, a communication interface, a display screen, and an input apparatus that are connected by using a system bus. The processor of the computer device is configured to provide computing and control capabilities. The memory of the computer device includes a non-volatile storage medium and an internal memory. The non-volatile storage medium stores an operating system and a computer-readable instruction. The internal memory provides an environment for running of the operating system and the computer-readable instruction in the non-volatile storage medium. The communication interface of the computer device is configured to communicate with an external terminal in a wired or a wireless manner, and the wireless manner can be implemented by using Wi-Fi, an operator network, NFC, or other technologies. The computer-readable instruction is executed by the processor to implement a method for classification processing of an electrophysiological signal. The display screen of the computer device may be a liquid crystal display screen or an electronic ink display screen. The input apparatus of the computer device may be a touch layer covering the display screen, or may be a key, a trackball, or a touch pad disposed on a housing of the computer device, or may be an external keyboard, a touch pad, a mouse, or the like.

Figure 14:
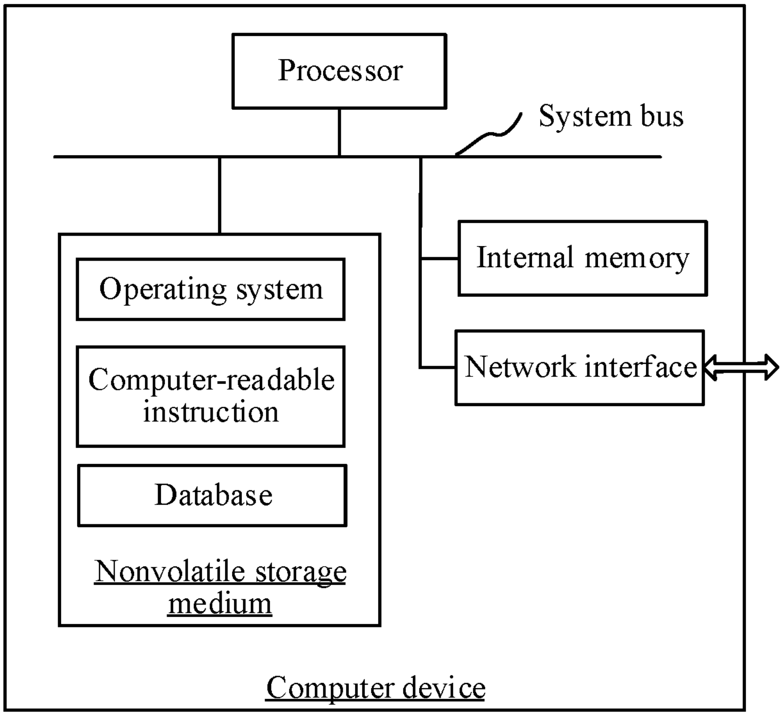
FIG. 14 is a diagram of an internal structure of a computer device according to an embodiment.
Figure 15:
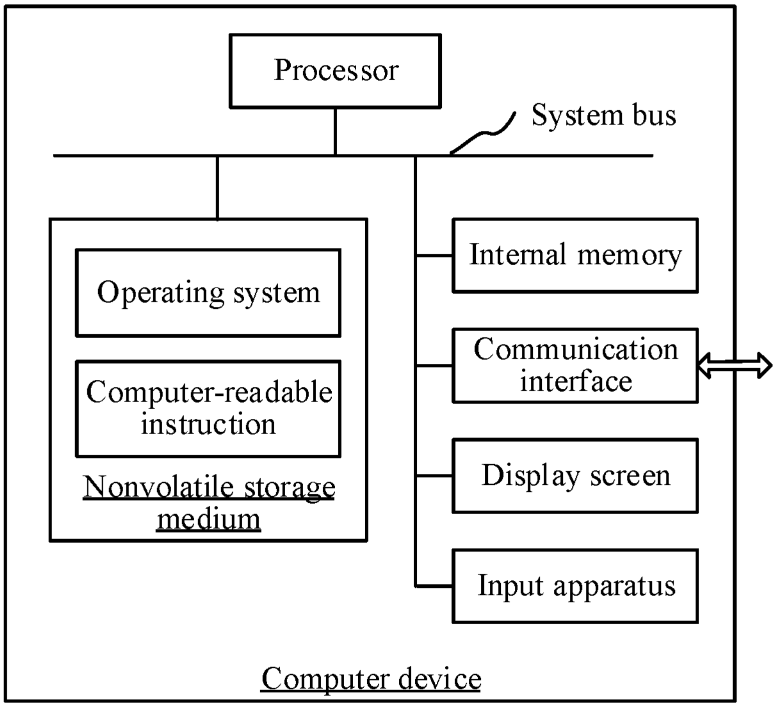
FIG. 15 is a diagram of an internal structure of a computer device according to an embodiment.

A person skilled in the art may understand that, the structure shown in FIGS. 14 and 15 is only a block diagram of a part of a structure related to a solution of the present disclosure and does not limit the computer device to which the solution of the present disclosure is applied. Specifically, the computer device may include more or fewer components than those in the drawings, or some components are combined, or a different component deployment is used.

In an embodiment, a computer device is further provided, including a memory and one or more processors, the memory storing computer-readable instructions, the one or more processors, when executing the computer-readable instructions, implementing the steps in the foregoing method embodiments.

In an embodiment, a computer-readable storage medium is provided, storing computer-readable instructions, the computer-readable instructions, when executed by one or more processors, implementing the steps in the foregoing method embodiments.

In an embodiment, a computer program product or a computer program is provided. The computer program product or computer program includes computer-readable instructions, the computer-readable instructions being stored in a computer-readable storage medium. The one or more processors of the computer device read the computer instructions from the computer-readable storage medium, and the one or more processors execute the computer instructions, to cause the computer device to perform the steps in the method embodiments.

A person of ordinary skill in the art may understand that all or some of the procedures of the methods of the foregoing embodiments may be implemented by computer-readable instructions instructing relevant hardware. The computer-readable instructions may be stored in a non-volatile computer-readable storage medium. When the computer-readable instructions are executed, the procedures of the embodiments of the foregoing methods may be included. Any reference to a memory, a storage, a database, or another medium used in the embodiments provided in the present disclosure may include at least one of a non-volatile memory and a volatile memory. The non-volatile memory may include a read-only memory (ROM), a magnetic tape, a floppy disk, a flash memory, an optical memory, and the like. The volatile memory may include a random access memory (RAM) or an external cache. For the purpose of description instead of limitation, the RAM is available in a plurality of forms, such as a static RAM (SRAM) or a dynamic RAM (DRAM).

The technical features in the foregoing embodiments may be combined in different manners to form other embodiments. For concise description, not all possible combinations of the technical features in the embodiment are described. However, provided that combinations of the technical features do not conflict with each other, the combinations of the technical features are considered as falling within the scope recorded in this specification.

The foregoing embodiments only describe several implementations of the present disclosure specifically and in detail, but cannot be construed as a limitation to the patent scope of the present disclosure. A person of ordinary skill in the art may make various changes and improvements without departing from the ideas of the present disclosure, which shall all fall within the protection scope of the present disclosure. Therefore, the protection scope of this patent application is subject to the protection scope of the appended claims.

What is claimed is:

1. A physiological electric signal classification processing method, performed by a computer device, the method comprising:

acquiring an initial physiological electric signal corresponding to a target user identity;

performing data alignment on the initial physiological electric signal based on target signal spatial information corresponding to the target user identify to obtain a target physiological electric signal;

performing spatial feature extraction on the target physiological electric signal based on a target spatial filtering matrix to obtain a target spatial feature, wherein the target spatial filtering matrix is generated by:

acquiring initial sample physiological electric signals corresponding to a plurality of training user identifies respectively, the initial sample physiological electric signals carrying training labels, each training user identity corresponding to a plurality of initial sample physiological electric signals;

performing initial sample physiological electric signal conversion based on a corresponding reference matrix generated from the plurality of initial sample physiological electric signals corresponding to the same training user identity, to obtain a target sample physiological electric signal corresponding to each training user identity; and generating the target spatial filtering matrix based on a signal difference between the target sample physiological electric signals corresponding to different training labels; and obtaining a classification result corresponding to the initial physiological electric signal based on the target spatial feature.

2. The method according to claim 1, wherein the acquiring an initial physiological electric signal corresponding to a target user identity comprises:

acquiring a candidate physiological electric signal corresponding to the target user identity;

performing signal extraction of at least one target frequency band for the candidate physiological electric signal to obtain an initial sub-signal corresponding to the candidate physiological electric signal at each target frequency band; and obtaining the initial physiological electric signal based on each initial sub-signal.

3. The method according to claim 1, wherein during the performing data alignment on the initial physiological electric signal based on target signal spatial information corresponding to the target user identify to obtain a target physiological electric signal, the method further comprises:

acquiring an initial reference matrix corresponding to the initial physiological electric signal;

modifying the initial reference matrix based on the initial physiological electric signal to obtain a modified reference matrix corresponding to the initial physiological electric signal; and using the modified reference matrix corresponding to the initial physiological electric signal as the target signal spatial information.

4. The method according to claim 3, wherein the initial reference matrix is a modified reference matrix corresponding to a previous physiological electric signal corresponding to the target user identity.

5. The method according to claim 3, wherein the modifying the initial reference matrix based on the initial physiological electric signal to obtain a modified reference matrix corresponding to the initial physiological electric signal comprises:

acquiring a number statistics result of classified physiological electric signals corresponding to the target user identity;

calculating a covariance matrix corresponding to the initial physiological electric signal; and modifying the initial reference matrix based on the number statistics result and the covariance matrix to obtain a modified reference matrix corresponding to the initial physiological electric signal.

6. The method according to claim 5, wherein the initial reference matrix comprises an initial reference sub-matrices corresponding to at least one target frequency band respectively, and the initial physiological electric signal comprises initial sub-signals corresponding to the at least one target frequency band respectively; and the modifying the initial reference matrix based on the number statistics result and the covariance matrix to obtain a modified reference matrix corresponding to the initial physiological electric signal comprises:

modifying the corresponding initial reference sub-matrix based on the initial sub-signals corresponding to the same target frequency band and the number statistics result to obtain a modified reference sub-matrix corresponding to each target frequency band; and obtaining the modified reference matrix based on each modified reference sub-matrix.

7. The method according to claim 3, wherein the modified reference matrix corresponding to the initial physiological electric signal comprises modified reference sub-matrices corresponding to at least one target frequency band respectively, and the initial physiological electric signal comprises initial sub-signals corresponding to the at least one target frequency band respectively; and the performing data alignment on the initial physiological electric signal based on target signal spatial information corresponding to the target user identify to obtain a target physiological electric signal comprises:

fusing the modified reference sub-matrix and the initial sub-signal corresponding to the same target frequency band to obtain a target sub-signal corresponding to each target frequency band; and obtaining the target physiological electric signal based on each target sub-signal.

8. The method according to claim 1, wherein the performing initial sample training physiological electric signal conversion comprises:

generating a corresponding initial reference matrix based on each initial sample physiological electric signal corresponding to the same training user identity to obtain the initial reference matrix corresponding to each training user identity using the initial reference matrix corresponding to the same training user identity as the corresponding reference matrix.

9. The method according to claim 8, wherein the initial sample physiological electric signal comprises initial training sub-signals corresponding to at least one target frequency band respectively, and the generating a corresponding initial reference matrix based on each initial sample physiological electric signal corresponding to the same training user identity to obtain the initial reference matrix corresponding to each training user identity comprises:

calculating an initial covariance matrix corresponding to each initial training sub-signal;

calculating a corresponding initial reference sub-matrix based on each initial covariance matrix corresponding to the same training user identity and the same target frequency band to obtain the initial reference sub-matrix corresponding to each training user identity at each target frequency band; and obtaining the initial reference matrix corresponding to each training user identity based on each initial reference sub-matrix.

10. The method according to claim 9, wherein the initial sample physiological electric signal comprises channel signals corresponding to a plurality of acquisition channels on a physiological electric signal acquisition device, and the initial training sub-signal comprises a channel sub-signal corresponding to each acquisition channel; and the calculating an initial covariance matrix corresponding to each initial training sub-signal comprises:

calculating a covariance between the channel sub-signals in a current initial training sub-signal; and generating an initial covariance matrix corresponding to the current initial training sub-signal based on the covariance between the channel sub-signals.

11. The method according to claim 1, wherein the initial reference matrix comprises initial reference sub-matrices corresponding to at least one target frequency band respectively, and the initial sample physiological electric signal comprises initial training sub-signals corresponding to the at least one target frequency band respectively; and the performing data alignment on a corresponding initial sample physiological electric signal based on training signal spatial information corresponding to the same training user identity to obtain a target sample physiological electric signal corresponding to each training user identity comprises:

fusing the initial reference sub-matrix and the initial training sub-signal corresponding to the same training user identity and the same target frequency band to obtain a target training sub-signal corresponding to each training user identity at each target frequency band; and obtaining the target sample physiological electric signal corresponding to each training user identity based on the target training sub-signal corresponding to each training user identity at each target frequency band.

12. The method according to claim 1, wherein the target sample physiological electric signal comprises target training sub-signals corresponding to at least one target frequency band respectively, and the generating the target spatial filtering matrix based on a signal difference between the target sample physiological electric signals corresponding to different training labels comprises:

generating a corresponding target spatial filtering sub-matrix based on a signal difference between target training sub-signals corresponding to different training labels in the same target frequency band to obtain the target spatial filtering sub-matrix corresponding to each target frequency band; and generating the target spatial filtering matrix based on each target spatial filtering sub-matrix.

13. The method according to claim 12, wherein the generating a corresponding target spatial filtering sub-matrix based on a signal difference between target training sub-signals corresponding to different training labels in the same target frequency band to obtain the target spatial filtering sub-matrix corresponding to each target frequency band comprises:

calculating a target covariance matrix corresponding to each target training sub-signal in a current target frequency band;

calculating a corresponding target reference matrix based on each target covariance matrix corresponding to the same training label to obtain the target reference matrix corresponding to each training label;

fusing all target reference matrices to obtain a fused reference matrix, and performing eigenvalue decomposition on the fused reference matrix to obtain an initial eigenvalue matrix and an initial eigenvector matrix corresponding to the fused reference matrix;

obtaining a whitening matrix based on the initial eigenvalue matrix and the initial eigenvector matrix;

performing whitening transformation on each target reference matrix based on the whitening matrix to obtain a transformed reference matrix corresponding to each target reference matrix;

performing eigenvalue decomposition on any one transformed reference matrix to obtain an eigenvalue decomposition result, and obtaining a target eigenvector matrix based on the eigenvalue decomposition result; and generating a target spatial filtering sub-matrix corresponding to the current target frequency band based on the whitening matrix and the target eigenvector matrix.

14. The method according to claim 13, wherein the generating a target spatial filtering sub-matrix corresponding to the current target frequency band based on the whitening matrix and the target eigenvector matrix comprises:

fusing the whitening matrix and the target eigenvector matrix to obtain an initial spatial filtering matrix;

extracting at least one initial spatial filtering sub-matrix from the initial spatial filtering matrix to obtain at least one initial spatial filtering sub-matrix; and obtaining the target spatial filtering sub-matrix based on each initial spatial filtering sub-matrix.

15. The method according to claim 1, wherein the target spatial filtering matrix comprises target spatial filtering sub-matrices corresponding to at least one target frequency band respectively, and the target physiological electric signal comprises target sub-signals corresponding to the at least one target frequency band respectively; and the performing spatial feature extraction on the target physiological electric signal based on a target spatial filtering matrix to obtain a target spatial feature comprises:

extracting a spatial feature of a corresponding target sub-signal based on a target spatial filtering sub-matrix corresponding to the same target frequency band to obtain a target spatial sub-feature corresponding to each target frequency band; and generating the target spatial feature based on each target spatial sub-feature.

16. The method according to claim 15, wherein the target spatial filtering sub-matrix comprises at least one initial spatial filtering sub-matrix, and the extracting a spatial feature of a corresponding target sub-signal based on a target spatial filtering sub-matrix corresponding to the same target frequency band to obtain a target spatial sub-feature corresponding to each target frequency band comprises:

performing signal projection on the corresponding target sub-signal based on each initial spatial filtering sub-matrix in a current target frequency band to obtain a target projection sub-signal corresponding to each target sub-signal;

calculating initial variance data corresponding to each target projection sub-signal;

performing normalization processing on the initial variance data to obtain corresponding target variance data; and obtaining the target spatial sub-feature corresponding to the current target frequency band based on the target variance data.

17. The method according to claim 1, wherein the obtaining a classification result corresponding to the initial physiological electric signal based on the target spatial feature comprises:

inputting the target spatial feature into a target physiological electric signal classification model to obtain the classification result, wherein a training process of the target physiological electric signal classification model comprises:

performing spatial feature extraction on each target sample physiological electric signal based on the target spatial filtering matrix to obtain a training spatial feature corresponding to each target sample physiological electric signal;

inputting each training spatial feature into an initial physiological electric signal classification model to obtain a prediction label corresponding to each target sample physiological electric signal; and adjusting model parameters of the initial physiological electric signal classification model based on the prediction label and training label corresponding to the same target sample physiological electric signal until a convergence condition is met to obtain the target physiological electric signal classification model.

18. A physiological electric signal classification processing apparatus, the apparatus comprising:

a memory and one or more processors, the memory storing computer-readable instructions, the one or more processors, when executing the computer-readable instructions, being configured to perform:

acquiring an initial physiological electric signal corresponding to a target user identity;

performing data alignment on the initial physiological electric signal based on target signal spatial information corresponding to the target user identify to obtain a target physiological electric signal;

performing spatial feature extraction on the target physiological electric signal based on a target spatial filtering matrix to obtain a target spatial feature, wherein the target spatial filtering matrix is generated by:

acquiring initial sample physiological electric signals corresponding to a plurality of training user identifies respectively, the initial sample physiological electric signals carrying training labels, each training user identity corresponding to a plurality of initial sample physiological electric signals;

performing initial sample physiological electric signal conversion based on a corresponding reference matrix generated from the plurality of initial sample physiological electric signals corresponding to the same training user identity, to obtain a target sample physiological electric signal corresponding to each training user identity; and generating the target spatial filtering matrix based on a signal difference between the target sample physiological electric signals corresponding to different training labels; and obtaining a classification result corresponding to the initial physiological electric signal based on the target spatial feature.

19. One or more non-transitory computer-readable storage medium, storing computer-readable instructions, the computer-readable instructions, when executed by one or more processors, implementing:

acquiring an initial physiological electric signal corresponding to a target user identity;

performing data alignment on the initial physiological electric signal based on target signal spatial information corresponding to the target user identify to obtain a target physiological electric signal;

performing spatial feature extraction on the target physiological electric signal based on a target spatial filtering matrix to obtain a target spatial feature, wherein the target spatial filtering matrix is generated by:

acquiring initial sample physiological electric signals corresponding to a plurality of training user identifies respectively, the initial sample physiological electric signals carrying training labels, each training user identity corresponding to a plurality of initial sample physiological electric signals;

performing initial sample physiological electric signal conversion based on a corresponding reference matrix generated from the plurality of initial sample physiological electric signals corresponding to the same training user identity, to obtain a target sample physiological electric signal corresponding to each training user identity; and generating the target spatial filtering matrix based on a signal difference between the target sample physiological electric signals corresponding to different training labels; and obtaining a classification result corresponding to the initial physiological electric signal based on the target spatial feature.

* * * * *